United States Patent [19]
Janulis et al.

[11] Patent Number: 5,437,812
[45] Date of Patent: * Aug. 1, 1995

[54] LIQUID CRYSTAL COMPOUNDS HAVING PERFLUOROETHER TERMINAL PORTIONS

[75] Inventors: Eugene P. Janulis, Mahtomedi; Gilbert C. Johnson, Anoka; Patricia M. Savu; Terence D. Spawn, both of Maplewood; Marc D. Radcliffe, Woodbury, all of Minn.

[73] Assignee: Minnesota Mining and Manufacturing Company, St. Paul, Minn.

[ * ] Notice: The portion of the term of this patent subsequent to Nov. 16, 2010 has been disclaimed.

[21] Appl. No.: 45,283

[22] Filed: Apr. 16, 1993

Related U.S. Application Data

[63] Continuation-in-part of Ser. No. 875,223, Apr. 28, 1992, Pat. No. 5,262,082.

[51] Int. Cl.⁶ .................. C09K 19/52; C09K 19/34; C07D 239/02; C07C 43/247; G07F 1/12
[52] U.S. Cl. .................. 252/299.01; 252/299.61; 252/299.66; 544/298; 568/647; 568/649; 359/104
[58] Field of Search .......... 252/299.01, 299.61, 252/49.62, 299.64, 299.65, 299.66, 299.67; 544/298; 568/647, 649; 359/104

[56] References Cited

U.S. PATENT DOCUMENTS

| | | | |
|---|---|---|---|
| 4,367,924 | 1/1983 | Clark et al. | 350/334 |
| 4,411,494 | 10/1983 | Crossland et al. | 350/339 |
| 4,419,664 | 12/1983 | Crossland et al. | 340/784 |
| 4,528,562 | 7/1985 | Crossland et al. | 340/805 |
| 4,886,619 | 12/1989 | Janulis | 252/299 |
| 5,051,527 | 9/1991 | Suzuki et al. | 560/51 |
| 5,082,587 | 1/1992 | Janulis | 252/299 |
| 5,087,672 | 2/1992 | Babirad et al. | 525/329 |
| 5,132,041 | 7/1992 | Cumming et al. | 252/299 |
| 5,262,082 | 11/1993 | Janulis et al. | 252/299.01 |

FOREIGN PATENT DOCUMENTS

| | | |
|---|---|---|
| 0405868 | 1/1991 | European Pat. Off. . |
| 0439190 | 7/1991 | European Pat. Off. . |
| 62-129251 | 6/1987 | Japan . |
| 3093748 | 4/1991 | Japan . |
| 4026679 | 1/1992 | Japan . |
| 9001021 | 2/1990 | WIPO . |
| 9001056 | 2/1990 | WIPO . |
| WO91/00897 | 1/1991 | WIPO . |

OTHER PUBLICATIONS

Kahn, F. J., *App. Phys. Lett.,* vol. 22, p. 111 (1973).
Lagerwall et al; 1st International Symposium on Ferroelectric Liquid Crystals, Bordeaux-Arcachon, France, 1987.
Pelzl, G. et al., *Kristall Technik,* vol. 14, p. 817 (1979).
Pelzl, G. et al., *Mol. Cryst. Liq. Cryst.* vol. 53, p. 167 (1979).
Pelzl, G. et al., *Liquis Crystals,* vol. 2, p. 21 (1987).
Pelzl, G. et al., *Liquid Crystals,* vol. 2, p. 131 (1987).
Meyer, R. B. et al., *J. Physique,* vol. 36, pp. 1–69 (1975).
Clark, N. A. et al., *Appl. Phys. Lett.,* vol. 36, p. 899 (1980).
Zaschke, H. and Stolle R, "Synthesis niedrigschmelzender, Kristallin-Flüssiger Hetercyclen; 5-n-Alk- (List continued on next page.)

*Primary Examiner*—Shean Wu
*Attorney, Agent, or Firm*—Gary L. Griwold; Walter N. Kirn; Carole Truesdale

[57] ABSTRACT

Fluorine-containing liquid crystal compounds are provided. The compounds comprise a fluorocarbon terminal portion having at least one catenary ether oxygen and a hydrocarbon terminal portion, the terminal portion being connected by a central core, the compounds having smectic mesophases or having latent smectic mesophases.

7 Claims, 1 Drawing Sheet

OTHER PUBLICATIONS yl-2-[4-n-alkanoyloxy-phenyl]pyrimidinr", *Z Chem.*, 15, pp. 441–443 (1975).

Partridge, M. W. and Short, W. F., *J. Chem. Soc.*, p. 390 (1947).

Arnold, Z. and Sorm F., *Coll. Czech. Chem. Commun.*, 23, p. 452 (1958).

Reiffenarath, V. et al., "New Liquid Crystalline Compounds With Negative Dielectric Anisotrophy", *Liquid Crystals*, 5, pp. 159–170 (1989).

Holy, A. and Arnold Z., *Coll. Czech. Chem. Commun.*, 38, p. 1372 (1973).

Hanack and Auchter, JACS 107 5238 (1985).

Y. Takanishi et al., "Spontaneous Formation of Quasi--Bookshelf Layer Structure in New Ferroelectric Liquid Crystals Derived from Naphthalene Ring", *Mol. Cryst. Liq. Cryst.*, vol. 199, pp. 111–118 (1991).

LIQUID CRYSTAL COMPOUNDS HAVING PERFLUOROETHER TERMINAL PORTIONS

This application is a continuation-in-part of application Ser. No. 07/875,223 filed Apr. 28, 1992 now U.S. Pat. No. 5,262,082.

FIELD OF THE INVENTION

This invention relates to fluorinated achiral smectic liquid crystal compounds. These compounds and mixtures of liquid crystal materials containing these compounds are useful in a variety of electrooptical displays.

BACKGROUND OF THE INVENTION

Devices employing liquid crystals have found use in a variety of electrooptical applications, in particular those which require compact, energy-efficient, voltage-controlled light valves, such as watch and calculator displays, and flat-panel displays as are found in portable computers and compact televisions.

Liquid crystal displays have a number of unique characteristics, including low voltage and low power of operation, which make them the most promising of the non-emissive electrooptical display candidates currently available. However, slow response and insufficient nonlinearity can impose limitations for many potential applications. The requirement for speed may become especially important in proportion to the number of elements which have to be addressed in a device. This limits the potential use of some types of liquid crystals.

The modes of liquid crystal displays that are most extensively employed at the present are twisted nematic (TN), supertwisted birefringence effect (SBE), and dynamic scattering (DS), all employing nematic or chiral nematic (cholesteric) liquid crystals. These devices are based upon the dielectric alignment effects (Freedericksz effect) of the nematic and/or chiral nematic liquid crystal or mixtures of nematic or chiral nematic liquid crystals upon application of an electric field. The average molecular long axis of the liquid crystal material takes up a preferred orientation in the applied electric field, the orientation of which is dependent on the sign of the dielectric anisotropy of the material or mixture, and this orientation relaxes upon removal of the applied electric field. This reorientation and relaxation is slow, on the order of a few milliseconds.

Although nematic and chiral nematic liquid crystals are the most extensively employed, there are liquid crystal devices that employ higher ordered smectic liquid crystals.

Devices employing materials with a smectic A mesophase are useful in device applications as described in Crossland, et al. U.S. Pat. Nos. 4,411,494; 4,419,664; and 4,528,562; and F. J. Kahn (Appl. Phys. Lett., vol. 22, p. 111 (1973). These devices are based on the dielectric reorientation of the liquid crystals and response times are on the order of milliseconds.

Mixtures which exhibit a chiral smectic A mesophase are useful in a device as described by Lagerwall, et al. 1st International Symposium On Ferroelectric Liquid Crystals, Bordeaux-Arcachon, France, 1987. These mixtures exhibit an electrooptic effect which is termed a soft-mode ferroelectric effect and sub-microsecond switching can be achieved.

Devices employing materials with a smectic C mesophase are useful in device applications as described by Pelzl, et al. (Kristall Technik., vol. 14, p. 817 (1979); Mol. Cryst. Liq. Cryst., vol. 53, p. 167 (1979); Liquid Crystals, vol. 2, p. 21 (1987); and Liquid Crystals, vol. 2, p. 131 (1987)). These devices are based on the dielectric reorientation of the liquid crystals and the response times are slow.

A recent advance in the liquid crystal art has been the utilization of tilted chiral smectic liquid crystals, which are also termed ferroelectric liquid crystals, in devices which give microsecond switching and bistable operation not possible in any of the device applications described above. Ferroelectric liquid crystals were discovered by R. B. Meyer, et al. (J. Physique, vol. 36, pp. 1–69, 1975). A high speed optical switching phenomenon was discovered for the ferroelectric liquid crystals by N. A. Clark, et al. (Appl. Phys. Lett., vol. 36, p. 899 (1980) and U.S. Pat. No. 4,367,924).

Fluorine-containing ferroelectric liquid crystal materials have recently been developed. U.S. Pat. No. 4,886,619 (Janulis) discloses fluorine-containing chiral smectic liquid crystal compounds which comprise a fluorocarbon terminal portion and a chiral hydrocarbon terminal portion with the terminal portions being connected by a central core. U.S. Pat. No. 5,082,587 (Janulis) discloses achiral fluorine-containing liquid crystal compounds which comprise a fluorocarbon terminal portion and a hydrocarbon or another fluorocarbon terminal portion, the terminal portions being connected by a central core.

International Publication No. WO 91/00897 (Merck) discloses chiral or achiral ring compounds which may be used as components of chiral, tilted, smectic liquid-crystalline phases with ferroelectric properties. The compounds have the formula

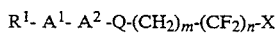

$$R^1\text{-}A^1\text{-}A^2\text{-}Q\text{-}(CH_2)_m\text{-}(CF_2)_n\text{-}X$$

where $R^1$ is an alkyl or perfluoroalkyl group with 1 to 12 carbon atoms, in which one or two non-adjacent $CH_2$ or $CF_2$ groups may be replaced by O-atoms, and/or -CO-, -COO-, -CH=CH-, -CH-halogen-, -CHCN-, -OCOCH-halogen-, or -COO-CHCN- groups or where $R^1$ is X-$(CF_2)_n$-$(CH_2)_m$-Q- and X is H or F; $A^1$ and $A^2$ are mutually independently unsubstituted 1,4-phenylene groups or 1,4-phenylene groups substituted by one or two F-atoms, whereby one or two CH-groups may may be substituted by N; Q is -O-, -COO-, -OCO- or a single bond; m is 1 to 10; and n is 2 to 8, with the proviso that m is 3 to 10 if Q is -COO- or -OCO-.

The high speed switching of the ferroelectric liquid crystals can be utilized in many applications: light valves, displays, printer heads, and the like. In addition to the submicrosecond switching speeds, some ferroelectric device geometries exhibit bistable, threshold sensitive switching, making them candidates for matrix addressed devices containing a large number of elements for passive displays of graphic and pictorial information, as well as optical processing applications.

SUMMARY OF THE INVENTION

The present invention provides fluorine-containing liquid crystal compounds comprising an aliphatic fluorocarbon terminal portion having at least one catenary ether oxygen and an aliphatic hydrocarbon terminal portion, the terminal portions being connected by a central core, the compounds having smectic mesophases or having latent smectic mesophases. Compounds having latent smectic mesophases are those which by themselves do not exhibit a smectic mesophase, but when the compounds are in admixture with said compounds having smectic mesophases or other said compounds having said latent smectic mesophases develop smectic mesophases, under appropriate conditions. The fluorocarbon terminal portion can be represented by the formula -D(C$_x$F$_{2x}$O)$_z$C$_y$F$_{2y+1}$ where x is 1 to 10, y is 1 to 10, z is 1 to 10 and D is a covalent bond,

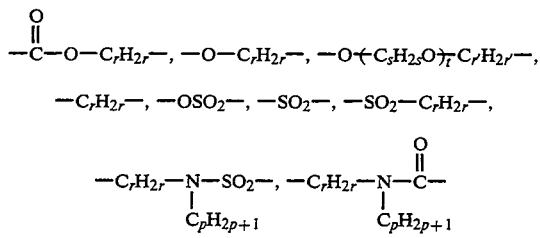

where r and r' are independently 1 to 20, s is independently 1 to 10 for each (C$_s$H$_{2s}$O), t is 1 to 6 and p is 0 to 4.

In general, the compounds of this invention have a central core comprised of at least two rings independently selected from aromatic, heteroaromatic, cycloaliphatic, or substituted aromatic, heteroaromatic, or cycloaliphatic rings, connected one with another by a covalent bond or by groups selected from -COO-, -COS-, -HC=N-, -COSe-. Rings may be fused or non-fused. Heteroatoms within the heteroaromatic ring comprise at least one atom selected from N, O, or S. Non-adjacent methylene groups in cycloaliphatic rings may be substituted by O or S atoms.

The fluorine-containing liquid crystal compounds having fluorocarbon terminal portions of the present invention are not optically active but are useful, for example, when used in mixtures with optically active liquid crystal materials. These compounds have a number of desirable properties when used in admixture with fluorinated ferroelectric liquid crystals with perfluoroaliphatic terminal portions such as those disclosed, for example, in U.S. Pat. No. 4,886,619 and U.S. Pat. No. 5,082,587. The compounds having perfluoroether terminal portions of the present invention possess lower temperature smectic A and C phases than compounds having perfluoroaliphatic terminal portions without an ether linkage having substantially the same number of carbon atoms in the terminal portion.

The inclusion of the liquid crystal compounds of the invention in mixtures with fluorinated ferroelectric liquid crystals with perfluoroaliphatic terminal portions results in compositions with lower viscosity and faster switching time than with mixtures without the liquid crystal compounds of the invention.

The presence of the compounds having perfluoroether terminal portions increases the temperature range of the smectic C phase of the admixture. A device containing such admixture will function only in the desired smectic C phase of the mixture. The compounds of the present invention having perfluoroether terminal portions have lower transitions from smectic C to higher order and, thus, act to prevent admixtures from going from smectic C to higher order until the admixture temperature is lower than that at which the compounds having perfluoroaliphatic terminal portions would normally change to higher order.

The fluorine-containing liquid crystal compounds having perfluoroether terminal portions also have good chemical stability towards water, weak acids and weak bases, do not undergo degradation during normal use in a liquid crystal display device, and are photochemically stable, that is, they do not easily undergo photochemical reactions. These compounds, due to the novel fluorocarbon terminal portion, have greatly enhanced smectogenic properties, lower birefringences, and lower viscosities than their non-fluorine-containing analogues.

These fluorinated liquid crystal compounds having perfluoroether terminal portions and mixtures which contain them are useful in a variety of electrooptical displays. In particular, these fluorinated materials exhibit smectic mesophases, especially smectic A and C, and are useful in the formulation of smectic A (SmA), smectic C (SmC), chiral smectic A (SmA*), and chiral smectic C (SmC*) mixtures.

DETAILED DESCRIPTION OF THE INVENTION

Figure 1:
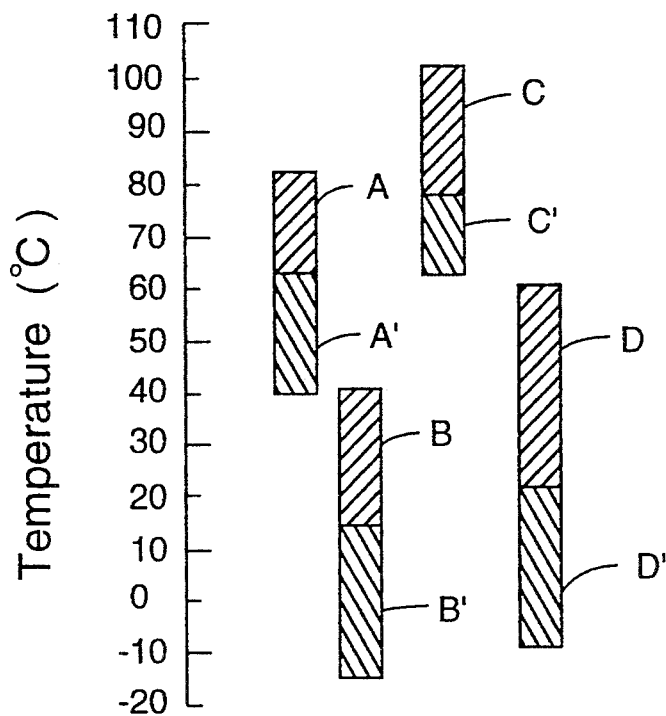
FIG. 1 shows comparative Smectic A and Smectic C phases for prior art liquid crystal materials and liquid crystal materials of the invention as determined by DSC.

The present invention relates to fluorine-containing liquid crystal compounds having perfluoroether terminal portions and mixtures derived therefrom which find use in smectic liquid crystal display applications and the like. The liquid crystals of the present invention can be represented by the general formula I:

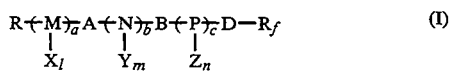

where M, N, and P are each independently

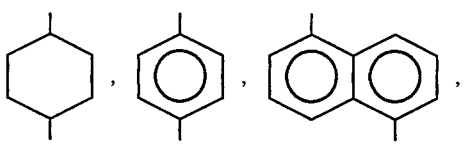

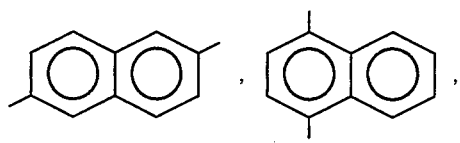

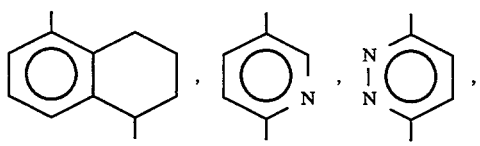

-continued

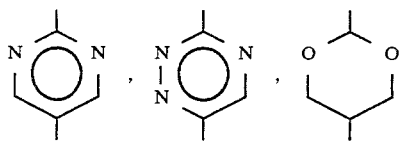

a, b, and c are each independently zero or an integer of from 1 to 3 with the proviso that the sum of a+b+c be at least 2;

each A and B are non-directionally and independently a covalent bond,

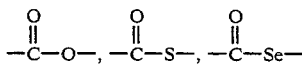

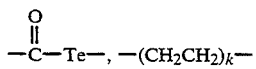

where k is 1 to 4,

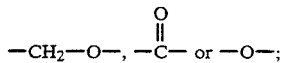

each X, Y, and Z are independently -H, -Cl, -F, -Br, -I, -OH, -OCH$_3$, -CH$_3$, -CF$_3$, -OCF$_3$ -CN, or -NO$_2$;

each l, m, and n are independently zero or an integer of 1 to 4,

D is a covalent bond,

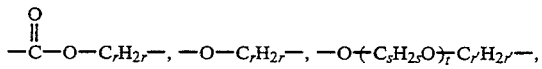

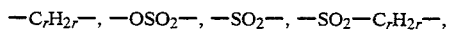

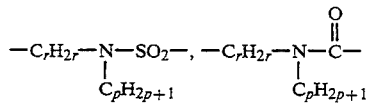

where r and r' are independently 1 to 20, s is independently 1 to 10 for each (C$_s$H$_{2s}$O), t is 1 to 6 and where r and r' are independently 1 to 20, and p is 0 to 4;

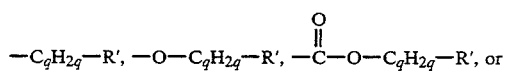

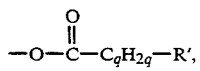

where R' is —Cl, —F, —CF$_3$, —NO$_2$, —CN, —H,

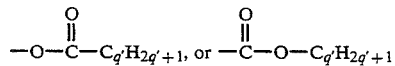

and q and q' are independently 1 to 20, w is 1 to 10 and R can be straight chain or branched; and R$_f$ is -(C$_x$F$_{2x}$O)$_z$C$_y$F$_{2y+1}$ where x is independently 1 to 10 for each C$_x$F$_{2x}$O, y is 1 to 10 and z is 1 to 10.

A preferred class of compounds of the invention have a pyrimidine core and can be represented by the formula

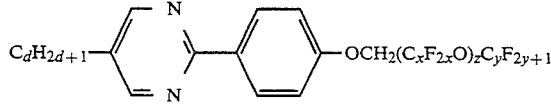

or

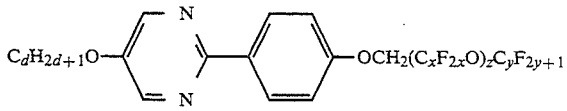

where d is 5 to 10, x is independently 1 to 3 for each C$_x$F$_{2x}$O, y is 1 to 4 and z is 1 to 3.

Compounds of the present invention have birefringences typically in the range of 0.05–0.18 depending on the ring systems present and the number of rings, suppressed nematic mesophases, i.e., exhibit no or very small nematic mesophase temperature ranges and enhanced smectic mesophases. Mixtures of the compounds of the invention with other liquid crystal materials can be formulated to provide desired transition temperatures and broad mesophase temperature ranges. Such mixtures preferably contain fluorine-containing chiral smectic liquid crystals as disclosed in U.S. Pat. No. 4,886,619 (Janulis) and/or achiral fluorine-containing liquid crystals as disclosed in U.S. Pat. No. 5,082,587, each of which is incorporated herein by reference.

The individual compounds of this invention which exhibit smectic A behavior can be used in admixture with other materials in smectic A device applications (see Crossland, et al. U.S. Pat. Nos. 4,411,494, 4,419,664, and 4,528,562, which are incorporated herein by reference, and F. J. Kahn (Appl. Phys. Lett., vol. 22, p. 111 (1973).

The individual compounds of this invention which exhibit smectic C behavior can be used in admixture with other materials in the smectic C Freedericksz device application described by Pelzl et al., (see Kristall Technik., vol. 14, p. 817 (1979); Mol. Cryst. Liq. Cryst., vol. 53, p. 167 (1979); Liquid Crystals, vol. 2, p. 21 (1987); and Liquid Crystals, vol. 2, p. 131 (1987)). As pointed out in the studies of Pelzl, et al. the decay time in the smectic C phase is shorter than in the nematic phase of the same material and in some cases the rise times are shorter, making this type of device application preferential to utilizing nematics in the classical Freedericksz device mode for some applications. The rise and decay times for the materials examined by Pelzl, et al. were on the order of 2–100 milliseconds for a 50% change in the measured light intensity. For materials of the present invention, rise and decay times of less than 1 millisecond have been observed for an 80% change in the light intensity. Rise and decay times of a few milliseconds for an 80% change in the light intensity have been observed in room temperature mixtures. Devices utilizing materials of the present invention make practical the use of smectic C materials in place of nematic materials in Freedericksz type devices and significantly shorter rise and decay times are attainable.

The compounds of this invention do not show chiral smectic (ferroelectric) liquid crystal behavior by themselves since they are achiral. However, a preferred embodiment of this invention comprises mixtures which contain materials of this invention with at least one chiral (optically active) component. The broad smectic C mesophase ranges and lower temperature smectic C mesophases of many of the materials of this invention make them useful and desirable as components in the formulation of broad smectic C eutectics, which become ferroelectric, or chiral smectic C, upon addition of a chiral additive. Those compounds of the invention having multiple ether oxygen atoms are capable of increasing the temperature range for broader eutectic ranges in mixtures. An ether oxygen link between the hydrocarbon terminal portion and the central core further increases the SmA to SmC transition temperature Other advantages of using the materials of this invention in the formulation of chiral smectic mixtures are the low birefringence and viscosity which can be obtained. The lower viscosity of these materials results in reduced response times for the ferroelectric switching for a given bulk polarization value. The lower birefringence of these materials allows the fabrication of devices with larger device spacings. These materials provide a reduced temperature dependence of the smectic interlayer spacing. This property provides a spontaneous generation of a bookshelf layer structure which is ideal for a ferroelectric liquid crystal device. Light transmission through a surface-stabilized ferroelectric device (as described in U.S. Pat. No. 4,367,924, which is incorporated by reference herein) with two polarizers is represented by the following equation:

$$I = I_o (\sin^2(4\Theta)) (\sin^2(\pi \Delta n d/\lambda))$$

where
$I_o$ = transmission through parallel polarizers
$\Theta$ = material tilt angle
$\Delta n$ = liquid crystal birefringence
$d$ = device spacing
$\lambda$ = wavelength of light used To maximize the transmission, both $\sin^2(4\Theta)$ and $\sin^2(\pi\Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd = \lambda/2$.

This demonstrates the criticality of the low birefringence of the materials of this invention. Low birefringence allows a larger device thickness, d for a given wavelength of light. Thus, a larger device spacing is possible while still maximizing transmission, allowing easier device construction.

The fluorine-containing liquid crystal compounds having perfluoroether terminal portions of the invention can be prepared by a process comprising the steps of (1) mixing at least one compound represented by the formula

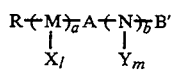

with at least one compound represented by the formula

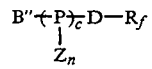

or (2) mixing at least one compound represented by the formula

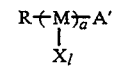

with at least one compound represented by the formula

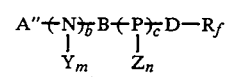

where M, N, and P are each independently

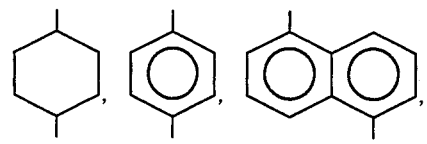

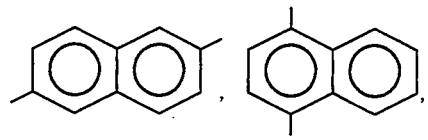

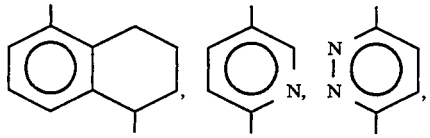

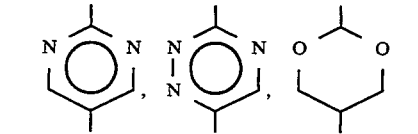

a, b, and c are each independently zero or an integer of from 1 to 3 with the proviso that the sum of a+b+c be at least 2;

each A and B are nondirectionally and independently a covalent bond,

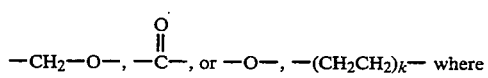

k is 1 to 4, —CH=CH—, or —C≡C—;

each A', A", B', and B" are independently -OH, -COOH, -CH(CH₂OH)₂, -SH, -SeH, -the, -NH₂, -COCl, -CHO, -OSO₂CF₃ or -CH₂COOH with the proviso that A' can enter into an addition or condensation reaction with A" and B' can enter into an addition or condensation reaction with B"; each X, Y, and Z are independently -H, -Cl, -F, -OCH₃, -OH, -CH₃, -CF₃, -OCF₃, -NO₂, -Br, -I, or -CN;

each l, m, and n are independently zero or an integer of 1 to 4;

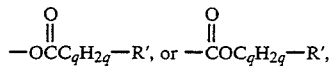

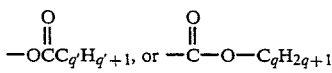

where R' is —H, —Cl, —F, —CF₃, —NO₂, —CN,

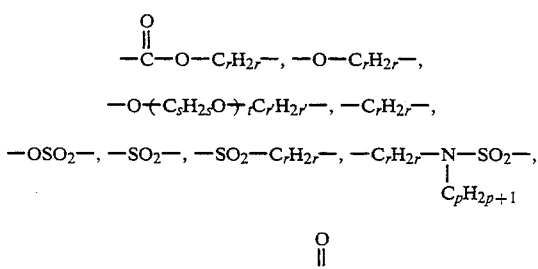

and q and q' are independently 1 to 20;

D is a covalent bond $$-\overset{O}{\underset{\|}{C}}-O-C_rH_{2r}-,\ -O-C_rH_{2r}-,$$

$$-O(-C_sH_{2s}O)_t-C_rH_{2r}-,\ -C_rH_{2r}-,$$

$$-OSO_2-,\ -SO_2-,\ -SO_2-C_rH_{2r}-,\ -C_rH_{2r}-\underset{\underset{C_pH_{2p+1}}{|}}{N}-SO_2-,$$

$$-CH_2)_r-\underset{\underset{C_pH_{2p+1}}{|}}{N}-\overset{O}{\underset{\|}{C}}-$$

where r and r' are independently 1 to 20, s is independently 1 to 10 for each (C$_s$H$_{2s}$O) , t is 1 to 6 and p is 0 to 4;

Rf is -(C$_x$F$_{2x}$O)$_z$C$_y$F$_{2y+1}$ where x is independently 1 to 10 for each C$_x$F$_{2x}$O group, y is 1 to 10 and z is 1 to 10; and allowing said A' and A" or B' and B" to react in the presence of suitable coupling agents, i.e., a reagent which effects coupling.

Objects and advantages of this invention are further illustrated by the following examples, but the particular materials and amounts thereof recited in these examples, as well as other conditions and details, should not be construed to unduly limit this invention.

In the following examples, all temperatures are in degrees Centigrade and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn were caused to react together to yield the achiral fluorine-containing liquid crystal compounds of this invention.

Compounds prepared in the various examples of this invention were characterized by their melting or boiling point and structures were confirmed by using at least one of the methods of analysis: chromatography, ¹³C- ¹H- and ¹⁹F-NMR, IR and MS spectroscopies Examples 1–35 describe procedures for preparing intermediate compounds useful in preparing the liquid crystal compounds of this invention. Examples 36–84 describe preparation of the liquid crystal compounds of this invention.

The 5-alkyl-2-(4-hydroxyphenyl)pyrimidines used in the examples were prepared using the method described by Zaschke, H. and Stolle, R. in "Synthese niedrigschmelzender Kristallin-Flüssiger Hetercyclen; 5-n-Alkyl- 2-[4-n-alkanoyloxy-phenyl]pyrimidine", Z. Chem., (15), pp. 441–443 (1975).

EXAMPLE 1

Cell drainings derived from the electrochemical fluorination of methyl 3-methoxypropanoate (45 g, 55% perfluoro-3-methoxypropionyl fluoride) were chilled to −78° C. in a dry ice acetone bath in a flask fitted with a −78° C. condenser, overhead stirrer, thermometer, and addition funnel. The exit line to the condenser was fitted with a drying tower. Over a period of 5 minutes, methanol (6 g) was added to the rapidly stirred solution. The flask was warmed to 0° C. and stirring was continued for one hour. At that time, the reaction mixture was allowed to warm to room temperature and then was stirred for an additional two hours. Water (100 mL) was added and the reaction mixture was allowed to phase split. The lower fluorochemical phase (40 g) was washed again with water (50 mL) to give 33 g of crude product. The crude product was added to a flask fitted with a 10.2 cm distillation column filled with steel helices and a distillation splitter. Polyphosphoric acid (9 g) was added to the distillation pot and the fluorochemical product was distilled. Two product cuts were obtained: boiling at 80-84° C. (5.2 g, 64% methyl perfluoro-3-methoxypropanoate), boiling at 84°-87° C. (6.5 g, 78% methyl perfluoro-3-methoxypropanoate). The GC-mass spectrum of the second product cut confirmed the identity of the major peak as CF₃OCF₂CF₂CO₂CH₃, methyl perfluoro-3-methoxypropanoate.

Sodium borohydride (5.0 g) was added to a flask fitted with a condenser, overhead stirrer, thermometer, and addition funnel. The sodium borohydride was slurried with 40 g of tetraglyme. With good stirring, the methyl perfluoro-3-methoxypropanoate (30.3 g) was added over a 30 minute period. The reaction mixture was heated at 90° C. for two hours. The reaction mixture was cooled to room temperature and poured into water (40 g). After the addition of the crude reaction product was complete, concentrated sulfuric acid (6.0 g) was added to the water/product mixture. The water/product mixture was returned to the flask and the product isolated by azeotropic distillation with water. A Barret trap was placed between the flask and the condenser. The crude reaction mixture was heated so that the product/water would distill into the trap. In the trap, the azeotrope split into two layers and the upper water layer was recycled to the flask. A total of 27.2 g of fluorochemical product was isolated from the trap. Karl Fischer water analysis showed the product to be 5.46 weight percent water. The product was added to polyphosphoric acid (23 g) and heated at 60° C. for one hour. The resultant product was one-plate distilled from the polyphosporic acid. The desired product (15.7 g) distilled at 96°-100° C. Analysis showed this material to be 0.1 weight percent water. F-NMR showed this material to contain the following: 91.1 mole% of the desired product, CF₃OCF₂CF₂CH₂OH, 1,1-dihydroheptafluoro-3-methoxypropanol, 6.0 mole% CF₃CF₂CH₂OH, and 1.2 mole % CF₃CF₂CF₂CH₂OH.

1,1-Dihydroheptafluoro-3-methoxypropanol (13.77 g, 0.0637 moles) and triethylamine (9.75 mL, 0.0701 moles) were dissolved in methylene chloride (25 mL) in a 100 mL flask fitted with a magnetic stir bar, low temperature thermometer, septum, and a nitrogen bubbler. The contents of the flask were then cooled to −20° C. and triflic anhydride (10.7 mL, 0.0637 moles) were added slowly via syringe to maintain the temperature below −15° C. After the addition was complete, the reaction was allowed to warm to room temperature. The solution was transferred to a separatory funnel and washed twice with 30 mL 0.5 N HCl and once with 30 mL water. The resulting solution was finally distilled and 8.75 mL of material boiling at 118°–120° C. were collected. GC showed 69 area % of the main component, 1,1-dihydroheptafluoro-3-methoxypropyl triflate.

EXAMPLE 2

Cell drainings derived from the electrochemical fluorination of ethoxyethyl acetate (235 g, 17% perfluoro-2-ethoxyacetyl fluoride) were chilled to −78° C. in a dry ice acetone bath in a flask fitted with a −78° C. condenser, overhead stirrer, thermometer, and addition funnel. The exit line to the condenser was fitted with a drying tower. Over a period of 5 minutes, methanol (12 g) was added to the rapidly stirred solution. The flask was warmed to 0° C. and stirring was continued for one hour. At that time, the reaction mixture was allowed to warm to room temperature and then was stirred overnight. Then, concentrated sulfuric acid (6 mL) was added and the reaction mixture phase-split. The lower fluorochemical phase was split away from the upper sulfuric acid/methanol/HF phase. A total of 101 g of crude product was isolated. GC showed this material to be 16 weight percent $CF_3CO_2CH_3$ and 26 weight percent $CF_3CF_2OCF_2CO_2CH_3$; gc/mass spectrum confirmed the identity of these peaks. The crude product was added to a flask fitted with a 10.2 cm distillation column filled with steel helices and a distillation splitter. Four product cuts were obtained: boiling at 65°–70° C. (5.8 g, 27% methyl perfluoro-2-ethoxyacetate), boiling at 70°–75° C. (6.4 g, 34% methyl perfluoro-2-ethoxyacetate), boiling at 75°–80° C. (16.8 g, 36% methyl perfluoro-2-ethoxyacetate), boiling at 80°–82° C. (16.1 g, 44% methyl perfluoro-2ethoxyacetate). The four product cuts were combined. The GC-mass spectrum of the blended product confirmed the identity of the major product peak as $CF_3CF_2OCF_2CO_2CH_3$, methyl perfluoro-2-ethoxyacetate.

Sodium borohydride (5.6 g) was added to a flask fitted with a condenser, overhead stirrer, thermometer, and addition funnel. The sodium borohydride was slurried with tetraglyme (45 g). With good stirring, the methyl perfluoro-2-ethoxyacetate (45.1 g, 37% methyl perfluoro-2-ethoxyacetate) was added over a 30 minute period. The reaction mixture was heated at 90° C. for two hours. The reaction mixture was cooled to room temperature and poured into water (80 g). After the addition of the crude reaction product was complete, concentrated sulfuric acid (7.2 g) was added to the water/product mixture. The water/product mixture was returned to the flask and the product isolated by azeotropic distillation with water. A Barret trap was placed between the flask and the condenser. The crude reaction mixture was heated to distill the product/water into the trap. In the trap, the azeotrope split into two layers and the upper water layer was recycled to the flask. A total of 20.5 g of fluorochemical product was isolated from the trap. Gas chromatography (GC) showed the product to be 66% desired product, $CF_3CF_2OCF_2CH_2OH$, 1,1-dihydroheptafluoro-2-ethoxyethanol. The GC/mass spectrum showed this material to consist of 73.8% $CF_3CF_2OCF_2CH_2OH$, 5.8% $CF_3OCF_2CH_2OH$ and 2.3% $CF_3CF_2OCF_2CF_2CH_2OH$.

1,1-Dihydro-heptafluoro-2-ethoxyethanol mixture, as described above (19.6 g, 82% fluorochemical alcohols), was dissolved in methylene chloride (30 mL) and dried with silica gel (0.9 g, 100–200 mesh, 983 grade) and filtered. The methylene chloride solution was placed in a flask fitted with a magnetic stirrer, thermometer, and addition funnel. Triethylamine (12.4 g) was added to the flask, and the internal temperature rose to 40° C. The flask was cooled to 5° C. in an ice bath, and then triflic anhydride (34.1 g) was added slowly so that the temperature did not exceed 10° C. The reaction mixture stirred overnight with warming to room temperature. Water (50 mL) and methylene chloride (20 mL) were added and the mixture allowed to phase split. The lower product phase was then washed with 3% sulfuric acid (50 mL) and water (20 mL). The methylene chloride was then stripped off at atmospheric pressure. The product cut distilled at a head temperature of 107°–115° C. A total of 10.4 g of product was obtained. The GC/mass spectrum showed this material to consist of 75.7 area % $CF_3CF_2OCF_2CH_2OSO_2CF_3$. F-NMR showed this material to consist of the following weight %: 87.0% $CF_3CF_2OCF_2CH_2OSO_2CF_3$, 4.6% $CF_3CF_2CF_2OCF_2CH_2OSO_2CF_3$, 0.3% $CF_3CF_2CF_2OCF_2CH_2OSO_2CF_3$.

EXAMPLE 3

Sodium borohydride (8.3 g) was added to a flask fitted with a condenser, overhead stirrer, thermometer, and addition funnel. The sodium borohydride was slurried with tetraglyme (100 g). With good stirring, methyl perfluoro-2-(butoxyethoxy)acetate (100 g, prepared by fluorination and methanolysis of butoxyethoxyethyl acetate) was added over a 30 minute period. The reaction mixture was heated at 90° C. for two hours and then cooled to 40° C. Methanol (18 g) was added slowly. The reaction mixture was heated at 50° C. for 30 minutes, then water (160 g) was rapidly added. After the addition of the water was complete, concentrated sulfuric acid (11 g) was added to the water/product mixture. The crude product was washed with water (160 g) to yield 95 g crude product. The crude product was distilled at 160 Pa (1.2 mm Hg) at a head temperature of 51°–60° C. to give 77.8 g of the desired product, 1,1-dihydroperfluoro-2-(butoxyethoxy) ethanol.

1,1-Dihydro-perfluoro-2-(butoxyethoxy)ethanol (10 g) was dissolved in methylene chloride (30 mL) and placed in a flask fitted with a magnetic stirrer, thermometer, and addition funnel. Triflic anhydride (8.1 g) was added to the flask. The flask was cooled to 5° C. in an ice bath, and then triethylamine (2.9 g) was added slowly so that the temperature did not exceed 10° C. The reaction mixture was stirred overnight with warming to room temperature. Water (20 mL) and methylene chloride (10 mL) were added and the mixture was allowed to phase split. The lower product phase was then washed with 3% sulfuric acid (20 mL) and water (10 mL). The methylene chloride was then stripped off atmospherically. The product cut distilled at a head temperature of 92°–95° C. at 60 kPa (45 mm Hg). A total of 9.4 g of product was obtained. GC/mass spectrum showed this material to consist of 88 area % of the desired product, $CF_3(CF_2)_3OCF_2CF_2OCF_2CH_2OSO_2CF_3$, 1,1-dihydroperfluoro-2(butoxyethoxy)ethyl triflate, and 10 area % $CF_3SO_2N(C_2H_5)_2$.

EXAMPLE 4

4-Cyano-4'-hydroxybiphenyl was converted to the corresponding amidine hydrochloride via the method of M. W. Partridge and W. F. Short (*J. Chem. Soc.*(1947), p. 390). The amidine hydrochloride (10 g, 0.0402 moles) and 2-octyl-3-dimethylaminoacrolein (8.5 g, 0.0402 moles, prepared as described by Z. Arnold, and F. Sorm, *Coll. Czech. Chem. Commun.*, 23(1958) p. 452) were then treated with 25% sodium methoxide in methanol (37 mL, 0.1608 moles) in 150 mL of absolute ethanol. The resulting mixture was heated to reflux and refluxed overnight. After cooling to room temperature, the solvent was removed under reduced pressure. Water (100 mL), ether (100 mL) and acetic acid (10 mL) were then added to the flask and the mixture was stirred until the solids dissolved. The resulting layers were separated. The aqueous layer was extracted twice with ether (50 mL). The combined ether layers were washed three times with water (50 mL), and dried with anhydrous magnesium sulfate. Finally, the solvent was removed under reduced pressure, and the resulting solid was recrystallized from hot acetonitrile to yield 5.38 g (37%) of the desired product, 5-octyl-2-(4'-hydroxybiphenyl)pyrimidine.

EXAMPLE 5

4-Benzyloxyphenol (10 g, 0.0499 moles) was slowly added to 60% sodium hydride in mineral oil (2.8 g) suspended in 100 mL of dry dimethoxyethane. After stirring the resulting solution for 30 minutes at room temperature, it was cooled with a dry ice/acetone bath. 1,1-dihydroheptafluoro-2-ethoxyethyl triflate (18 g, Example 2) was then added slowly. When the addition was complete, the ice bath was removed, and the mixture was stirred at room temperature overnight. The solvent was then removed under reduced pressure and water (200 mL), and ether (150 mL) were added. When the solids had dissolved, the layers were separated and the aqueous layer was extracted twice with ether (150 mL). The combined ether layers were washed once with 1 N sodium hydroxide (125 mL) and twice with water (150 mL), dried with anhydrous magnesium sulfate, and stripped to dryness on a rotary evaporator. The resulting solid (13 g) was dissolved in ethanol and hydrogenated at 0.4 MPa (60 psi) in the presence of catalytic 10% palladium on carbon for 18 hours. When the hydrogenation was complete the catalyst was removed by filtration, and the solvent was removed on a rotary evaporator. The resulting solid (6.5 g) was recrystallized from petroleum ether to yield 4 g of 4-(1,1-dihydroheptafluoro-2-ethoxyethoxy)phenol.

EXAMPLE 6

In this example, a compound was prepared in the same manner as that described in Example 5, except that 1,1-dihydroperfluoro-2-(butoxyethoxy)ethyl triflate (28 g, 0.049 moles) was substituted for the 1,1-dihydroheptafluoro-2-ethoxyethyl triflate, to provide 7.6 g of 4-(1,1-dihydroperfluoro-2-(butoxyethoxy)ethoxy)phenol.

EXAMPLE 7

4'-Benzyloxy-4-hydroxybiphenyl (1.5 g, 0.0054 moles) was slowly added to 60% sodium hydride in mineral oil (0.3 g) suspended in dry dimethoxyethane (15 mL). After stirring the resulting solution for 20 minutes at room temperature, it was cooled with an ice bath. 1,1-Dihydroheptafluoro-2-ethoxyethyl triflate (1.9 g, 0.0055 moles) was then added slowly. When the addition was complete, the ice bath was removed, and the mixture stirred at room temperature overnight. The solvent was then removed under reduced pressure, and water (25 mL) and ethyl ether (25 mL) were added. When the solids had dissolved, the layers were separated and the aqueous layer was extracted three times with ether (15 mL). The combined ether layers were washed three times with water (20 mL), dried with anhydrous magnesium sulfate, and solvent removed on a rotary evaporator. The resulting solid was dissolved in tetrahydrofuran and hydrogenated at 0.4 MPa (60 psi) in the presence of catalytic 10% palladium on carbon for 18 hours. When the hydrogenation was complete the catalyst was removed by filtration, and the solvent was removed on a rotary evaporator. The resulting solid was recrystallized from hexane to yield 1.2 g of 4'-(1,1-dihydroheptafluoro-2-ethoxyethoxy)-4-hydroxybiphenyl.

EXAMPLE 8

In this example, a compound was prepared in the same manner as that described in Example 7, utilizing 0.3 g of 60% sodium hydride in mineral oil, 15 mL of dimethoxyethane, 1.0 g (0.0036 moles) of 4'-benzyloxy-4-hydroxybiphenyl, except that 1,1-dihydroperfluoro-2-(butoxyethoxy)ethyl triflate (2.3 g, 0.0040 moles) was substituted for the 1,1-dihydroheptafluoro-2-ethoxyethyl triflate, to provide 1.0 g of 4'-(1,1-dihydroperfluoro-2-(butoxyethoxy)ethoxy)-4-hydroxybiphenyl.

EXAMPLE 9

6-Benzyloxy-2-napthol (2.5 g, 0.010 moles) was slowly added to 60% sodium hydride in mineral oil (0.7 g) suspended in dry dimethoxyethane (25 mL). After stirring the resulting solution for 20 minutes at room temperature, it was cooled with an ice bath. 1,1-Dihydroheptafluoro-2-ethoxyethyl triflate (3.8 g, 0.011 moles) was then added slowly. When the addition was complete, the ice bath was removed and the mixture was stirred at room temperature overnight. The solvent was then removed under reduced pressure and water (30 mL) and ether (30 mL) were added. When the solids had dissolved, the layers were separated and the aqueous layer was extracted twice with ether (25 mL). The combined ether layers were washed three times with water (20 mL), dried with anhydrous magnesium sulfate and stripped to dryness on a rotary evaporator. The resulting solid was dissolved in tetrahydrofuran and hydrogenated at 0.4 MPa (60 psi) in the presence of catalytic 10% palladium on carbon for 18 hours. When the hydrogenation was complete the catalyst was removed by filtration, and the solvent was removed on a rotary evaporator. The resulting solid was recrystallized from hexane to yield 1.28 g of 6-(1,1-dihydroheptafluoro-2-ethoxyethoxy)-2-hydroxynapthalene.

EXAMPLE 10

In this example, a compound was prepared in the same manner as that described in Example 9, except that 1,1-dihydroperfluoro-2-(butoxyethoxy)ethyl triflate (6.2 g, 0.010 moles) was substituted for the 1,1-dihydroheptafluoro-2-ethoxyethyl triflate, to provide 2.5 g of 6-(1,1-dihydroperfluoro-2-(butoxyethoxy)ethoxy)-2-hydroxynapthalene.

EXAMPLE 11

Sodium hydride (0.39 g of 80% suspension in mineral oil) was added to dimethyl formamide (5 mL) in a three-necked flask under an inert atmosphere. Methyl hydroxybenzoate (1.96 g, 0.129 moles) was dissolved in a mixture of toluene (10 mL) and dimethyl formamide (5 mL). The methyl hydroxybenzoate solution was added to the sodium hydride over a period of 15 minutes. The reaction was allowed to stir at room temperature for one hour. 1,1-Dihydroheptafluoro-2-ethoxyethyl triflate (4.5 g, 0.129 moles) was then added and the flask was heated to 116° C. for one hour. The reaction mixture was cooled to room temperature and poured into water (25 mL). The upper product phase was split off and rewashed with additional water (25 mL). The crude product solution was then stripped at 26.7 Pa (0.2 mm Hg) until the pot temperature reached 120° C. The product was then distilled at 4 Pa (0.03 mm Hg). The product (3.7 g) distilled at 100°–105° C. head temperature and consisted of a white low melting solid. GC-mass spectrum showed the material to consist of 89% of the product, methyl 4-(2,2-difluoro-2-pentafluoroethoxyethoxy)benzoate, with a molecular weight of 350, 5% of a material with a molecular weight of 430, and 6% of the starting methyl hydroxybenzoate. The infrared spectrum was consistent with the desired structure.

Subsequently, the methyl 4-(2,2-difluoro-2-pentafluoroethoxyethoxy)benzoate (3.3 g) was heated at reflux with 10% KOH (20 mL) for 2 hours. The hydrolysis reaction was then cooled to room temperature, and acidified with 98% sulfuric acid (1.75 g). The fluorinated benzoic acid precipitated, was isolated by filtration and washed twice with water (10 mL). The crude acid was then stirred with ethanol (50 mL) and filtered. The cake was washed with an additional 25 mL of ethanol. The material was dried in a vacuum oven at room temperature and 26.7 Pa (0.2 mm Hg). The desired 4-(1,1-dihydroheptafluoro-2-ethoxyethoxy)benzoic acid (2.7 g) was isolated.

EXAMPLE 12

Sodium (1.15 g, 50 mmoles) was reacted with anhydrous ethanol (200 mL) under a nitrogen atmosphere. 2,3-dicyanohydroquinone (8.01 g, 50 mmoles) in anhydrous ethanol (50 mL) was added dropwise to the ethoxide solution. Upon completion of the addition, potassium iodide (0.5 g) in 5 mL water was added. This solution was brought to reflux and octyl bromide (9.66 g, 50 mmoles) was added dropwise. The reaction was then refluxed under nitrogen atmosphere for one day. The mixture was acidified with 0.5N aqueous HCl and the solvents were removed under reduced pressure. The crude reaction mixture was flash chromatographed using silica gel and methylene chloride as eluent. The appropriate fractions containing the desired product, 2,3-dicyano-4-octyloxyphenol, were combined and the solvent removed under reduced pressure on a rotary evaporator. The crude product was recrystallized from ethanol/water to give 4.5 g 2,3-dicyano-4-octyloxyphenol.

EXAMPLE 13

2,3-Difluoro-4-octyloxyphenol was prepared as described in Reiffenrath, V. et al., "New Liquid Crystalline Compounds With Negative Dielectric Anisotrophy" *Liquid Crystals*, 5, (1989), pp. 159–170.

EXAMPLE 14

1,1-Dihydroperfluoro-2-(2-hexyloxyethoxy)ethyl triflate ($C_6F_{13}OC_2F_4OCF_2CH_2OSO_2CF_3$, bp 90°–100° C. at 3.0 mm Hg) was prepared from methyl perfluoro-2-(hexyloxyethoxy) ethanoate and 1,1-dihydroperfluoro-2-(2-hexyloxyethoxy)ethanol (bp 80°–85° C. at 3.5 mm Hg) as described in Example 3.

EXAMPLE 15

1,1-Dihydroperfluoro-4-(4-butoxybutoxy)butyl triflate ($C_4F_9OC_4F_8OC_3F_6CH_2OSO_2CF_3$, bp 76°–80° C. at 0.1 mm Hg) was prepared from methyl perfluoro-4-(4-butoxybutoxy) butanoate and 1,1-dihydroperfluoro-4-(4butoxybutoxy)butanol (bp 87°–100° C. at 3 mm Hg) as described in Example 3.

EXAMPLE 16

1,1-Dihydroperfluoro-2-(2-(2-methoxyethoxy)ethoxy) ethyl triflate ($CF_3O(C_2F_4O)_2CF_2CH_2OSO_2CF_3$, bp 70°–73° C. at 15 mm Hg) was prepared from methyl perfluoro-2-(2-(2-methoxyethoxy)ethoxy) ethanoate and 1,1-dihydroperfluoro-2-(2-(2-methoxyethoxy) ethoxy) ethanol (bp 72°–75° C. at 15 mm Hg) as described in Example 3.

EXAMPLE 17

1,1-Dihydroperfluoro-3-(butoxy)propyl triflate ($C_4F_9OC_2F_4CH_2OSO_2CF_3$, bp 73° C. at 15 mm Hg) was prepared from methyl perfluoro-3-(butoxy) propanoate and 1,1-dihydroperfluoro-f3-(butoxy) propanol (bp 60° C. at 15 mm Hg) as described in Example 3.

EXAMPLE 18

1,1-Dihydroperfluoro-4-(butoxy)butyl triflate ($C_4F_9OC_3F_6CH_2OSO_2CF_3$, bp 57°–63° C. at 2.5 mm Hg) was prepared from methyl perfluoro-4-(butoxy)-butanoate and 1,1-dihydroperfluoro-4-(butoxy)butanol as described in Example 3.

EXAMPLE 19

1,1-Dihydroperfluoro-3-(hexyloxy)propyl triflate ($C_6F_{13}OC_2F_4CH_2OSO_2CF_3$, bp 65°–67° C. at 0.1 mm Hg) was prepared from methyl perfluoro-3-(hexyloxy) propanoate and 1,1-dihydroperfluoro-3-(hexyloxy) propanol as described in Example 3.

EXAMPLE 20

1,1-Dihydroperfluoro-3-(octyloxy)propyl triflate ($C_8F_{19}OC_2F_4CH_2OSO_2CF_3$, bp 56° C. at 1 mm Hg) was prepared from methyl perfluoro-3-(octyloxy) propanoate and 1,1-dihydroperfluoro-3-(octyloxy) propanol as described in Example 3.

EXAMPLE 21

1,1-Dihydroperfluoro-3-(decyloxy)propyl triflate ($C_{10}F_{21}OC_2F_4CH_2 0SO_2CF_3$, bp 130°–140° C. at 9 mm Hg) was prepared from methyl perfluoro-3-(decyloxy) propanoate and 1,1-dihydroperfluoro-3-(decyloxy) propanol as described in Example 3.

EXAMPLE 22

1,1-Dihydroperfluoro-3-(neopentoxy)propyl triflate (($CF_3)_3CCF_2OC_2F_4CH_2OSO_2CF_3$) was prepared from methyl perfluoro-3-(neopentoxy) propanoate and 1,1-dihydroperfluoro-3-(neopentoxy) propanol as described in Example 3.

EXAMPLE 23

Ethylene carbonate (1.0 g, 11.6 mmol) was added to a stirred solution of 1,1-dihydroperfluoro-2-(2-butoxyethoxy)ethanol (5.0 g, 11.6 mmol) and potassium hydroxide (7 mg, 0.12 mmol) in tetraglyme (2 ml). The solution was heated to 100° C. for 6 hours and then at ambient temperature for 10 hours. The product was distilled from the reaction mixture to give 3.66 g of 2-[1,1-dihydroperfluoro-2-(2-butoxyethoxy)ethoxy] ethanol (bp 52° C. at 0.8 mm Hg) as a clear oil. Alcohol (3.66 g, 7.7 mmol) was then added to a stirred solution of 4-N,N dimethylaminopyridine (90 mg, 0.8 mmol), triethylamine (2.1 ml, 15.4mmol) and p-toluene sulfonyl chloride (1.61g, 8.5 mmol) in dichloromethane (20 ml). The solution was stirred under a nitrogen atmosphere for 10 hours and was then filtered through a pad of silica gel (20 g) (washed through with 100 ml of 4:1 hexane/ethyl acetate). The filtrate was concentrated to give the desired product, 2-[1,1-dihydroperfluoro-2-(2-butoxyethoxy)ethoxy]ethyl-p-toluenesulfonate

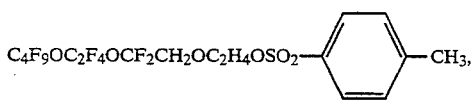

as a slightly browned oil.

EXAMPLE 24

2-(1,1-Dihydroperfluorooctyloxy)ethanol ($C_7F_{15}CH_2OCH_2CH_2OH$) was prepared by heating 1,1 dihydroperfluorooctanol (141.9 g), ethylene carbonate (51.7 g) and triethylamine (36.7 g) under reflux in an inert atmosphere (bath temperature 100° C.) for 36 hours. At that time, gas chromatography showed a mixture of 86% of the desired product, 4% starting alcohol, and 6% diadduct, with the balance being volatile impurities. Aqueous acidic workup with Freon 113 as the extraction solvent gave crude product. Vacuum distillation at aspirator pressure yielded forefractions containing 90% product, 68.1 g, and a center cut of 99% purity, 41.8 g.

EXAMPLE 25

2-(1,1-Dihydroperfluorohexyloxy)ethanol ($C_5F_{11}CH_2OCH_2CH_2OH$) was prepared as described in Example 24 except 1,1-dihydroperfluorohexanol was substituted for the 1,1-dihydro-perfluorooctanol.

EXAMPLE 26

2-(2-(1,1-Dihydroperfluorooctyloxy)ethoxy)ethanol ($C_7F_{15}CH_2OCH_2CH_2OCH_2CH_2OH$) was prepared by heating 2-(1,1-dihydroperfluorooctyloxy)ethanol (53 g) (Example 24), ethylene carbonate (46.4 g) and triethylamine (33.8 g) under inert atmosphere. The mixture was heated at reflux for 5 days. Aqueous acidic workup with Freon 113 as the extraction solvent gave crude product. The product was distilled (kugelrohr) to give 13.63 g of the desired product.

EXAMPLE 27

1-Bromo-2-(1,1 dihydroperfluorooctyloxy)ethane ($C_7F_{15}CH_2OCH_2CH_2Br$) was prepared as described in Hanack and Auchter, JACS 107 5238 (1985). A 50 ml flask fitted with magnetic stirring, inert atmosphere, thermometer, and septum inlet was charged with triphenylphosphine (6.22 g) and acetonitrile (25 ml). The flask was chilled in an ice-salt bath to a solution temperature of −3° C. and bromine, 3.76 g, was added by gastight syringe over 15 minutes, maintaining a solution temperature of less than 5° C. After an additional 5 minutes, the bath was removed and 2-(1,1-dihydroperfluorooctyloxy) ethanol (Example 24) (10.0 g) was added by syringe over about 7 minutes. After one hour, the reaction was worked up in water, dichloromethane as the extraction solvent, dried and solvent removed to yield a mixture of product and triphenylphosphine oxide byproduct. Trituration with Freon 113 yielded crude product as a colorless oil, from which separated a small amount of the triphenylphosphine oxide byproduct. Filtration gave 11.65 g product (11.42 g theoretical yield). No further purification was carried out.

EXAMPLE 28

1,1-Dihydroperfluorohexyl 2-bromoethyl ether, ($C_5F_{11}CH_2OCH_2CH_2Br$) was prepared as in Example 27, except 2-(1,1-dihydroperfluorohexyloxy) ethanol was substituted for the 2-(1,1-dihydroperfluoroocytloxy)ethanol.

EXAMPLE 29

1-Bromo-2-(2-(1,1-dihydroperfluorooctyloxy)-ethoxy)ethane ($C_7F_{15}CH_2OCH_2CH_2OCH_2CH_2Br$) was prepared as in Example 27 except 2-(2-(1,1-dihydroperfluorooctyloxy)ethoxy)ethanol was substituted for the 2-(1,1-dihydroperfluorooctyloxy)ethanol.

EXAMPLE 30

In a one-liter flask, 30 g (0.09 moles) of 2-benzyloxytrimethinium perchloroate (prepared according to the procedure of A. Holy and Z. Arnold, Collection Czechoslov. Chem. Commun., 38 (1973) 1372), 15.6 g (0.09 moles) para-hydroxybenzamidine hydrochloride, 82.5 ml (0.36 moles) of 25% sodium methoxide in methanol, and 500 ml of ethanol were combined. The mixture was heated to reflux overnight, and then cooled to room temperature. Then, 75 ml of acetic acid and 300 ml of water was added to the flask, resulting in the precipitation of the product. The product was collected by filtration, washed with water and air dried. The yield of 5-benzyloxy-2-(4-hydroxyphenyl)pyrimidine was 23.06 g (92%).

EXAMPLE 31

In a one-liter flask, 16.5 g (0.05 moles) of 2-benzyloxytrimethinium perchloroate (prepared according to the procedure of A. Holy and Z. Arnold, Collection Czechoslov. Chem. Commun., 38 (1973) 1372), 12.3 g (0.05 moles) 4'-hydroxyphenylbenzamidine hydrochloride, 45 ml (0.20 moles) of 25% sodium methoxide in methanol, and 300 ml of methanol were combined. The mixture was heated to reflux overnight, and then cooled to room temperature. To the flask were added 300 ml of water, which resulted in precipitate formation. Most of the methanol was removed under vacuum on a rotary evaporator. The solid was collected by filtration. The cake was dissolved in 95° C. water and the hot solution was acidified with concentrated hydrochloric acid to precipitate the product. The product was collected by filtration from the hot mixture, washed with warm water, and air dried. The yield of 5-benzyloxy-2-(4'-hydroxybiphenyl)pyrimidine was 11.97 g (68%).

EXAMPLE 32

5-Benzyloxy-2-(4-hydroxyphenyl)pyrimidine (18 g, 0.0647 moles, Example 30) was dissolved in 150 ml of N,N-dimethylformamide in a 500 ml flask, and 1.7 g of dry sodium hydride was added. After stirring the mixture for 15 minutes, 36.5 g (0.0647 moles) of 1,1-dihydroperfluoro-2-(butoxyethoxy)ethyltriflate was added and the mixture was heated to 95° C. for 1 hour. Upon cooling to room temperature, an equal volume of water was added. The resulting solid was collected by filtration. The solid was then slurried in boiling methanol, cooled to room temperature, and again collected by filtration. The solid was hydrogenated on a Parr Hydrogenator with catalytic 10% palladium on carbon in tetrahydrofuran under 413.7 kPa hydrogen pressure for about 18 hours. When the hydrogenation was complete, the catalyst was removed by filtration and the solvent was removed on a rotary evaporator to yield 25.62 g (66% yield) of 5-hydroxy-2-(4-(1,1-dihydroperfluro-2-(butoxyethoxy)ethoxy)phenyl)pyrimidine.

EXAMPLE 33

5-Hydroxy-2-(4-(1,1-dihydroperfluro-2-(butoxy)ethoxy)phenyl) pyrimidine was prepared as described in Example 32 except that 1,1-dihydroperfluro-2-(butoxy)ethyltriflate was substituted for 1,1-dihydroperfluoro-2-(butoxyethoxy)ethyltriflate.

EXAMPLE 34

5-Benzyloxy-2- (4-hydroxyphenyl) pyrimidine ( 2 g, 0.0072 moles, Example 30) was dissolved in 15 ml of N,N-dimethylformamide in a 50 ml flask and 0.2 g of dry sodium hydride was added. After stirring the mixture for 15 minutes, 1.39 g (0.0072 moles) of octylbromide was added and the mixture was heated to 100° C. for 2 hours. Upon cooling to room temperature, 15 ml of water was added. The resulting solid was collected by filtration and the solid was then slurried in boiling methanol, cooled to room temperature, and again collected by filtration. The solid was hydrogenated on a Parr Hydrogenator with catalytic 10% palladium on carbon in tetrahydrofuran under 413.7 kPa hydrogen pressure for about 18 hours. When the hydrogenation was complete, the catalyst was removed by filtration, and the solvent was removed on a rotary evaporator to yield 1.62 g (75% yield) of 5-hydroxy-2-(4-(octyloxy)phenyl)pyrimidine.

EXAMPLE 35

5-Hydroxy-2-(4'-(1,1-dihydroperfluro-2-(butoxyethoxy)ethoxy) biphenyl)pyrimidine was prepared as described in Example 32 except that 5-benzyloxy-2-(4'-hydroxybiphenyl)pyrimidine (Example 31) was substituted for 5-benzyloxy-2-(4-hydroxyphenyl)pyrimidine.

EXAMPLE 36

A 100 mL 3-neck flask fitted with a magnetic stir bar, septum, stopper, and water cooled condenser connected to a nitrogen bubbler was charged with dry sodium hydride (0.8 g, 0.0345 moles), toluene (20 mL), and dimethyl formamide (20 mL). With vigorous stirring, 5-hexyl-2-(4-hydroxyphenyl)pyrimidine (5.9 g, 0.023 moles) was added slowly to control the hydrogen evolution. The resulting mixture was stirred at room temperature for 30 minutes. Then, 1,1-dihydroheptafluoro-3-methoxypropyl triflate (8 g, 0.023 moles, prepared in Example 1) was added and the solution was heated to reflux. After 1 hour, the reaction mixture was allowed to cool to room temperature. The contents of the flask were poured into a separatory funnel containing water (50 mL). The resulting layers were separated and the aqueous layer was extracted twice with toluene (20 mL). The combined organic layers were then washed three times with water, dried with anhydrous sodium sulfate, and filtered. After solvent removal on a rotary evaporator, a brown oil resulted. This oil was chromatographed on silica gel (125 g), eluting with chloroform. Care was taken to separate the product from a yellow impurity which eluted off the column just before and overlapping with the desired product. A pale yellow semisolid (liquid crystalline at room temperature) resulted. The yield of this desired product, 5-hexyl-2-(4-(1,1-dihydroheptafluoro-3-methoxypropoxy)phenyl)pyrimidine, Compound 1, Table 1, was 2.8 g.

EXAMPLE 37

A 100 mL 3-neck flask fitted with a magnetic stir bar, septum, stopper, and water cooled condenser connected to a nitrogen bubbler was charged with. 60% sodium hydride/mineral oil (1.6 g, 0.04 moles), toluene (25 mL), and dimethyl formamide (25 mL). With vigorous stirring, 5-octyl-2-(4-hydroxyphenyl)pyrimidine (7.6 g, 0.0267 moles) was added slowly to control the hydrogen evolution. The resulting mixture was stirred at room temperature for 30 minutes. Then, 1,1-dihydroheptafluoro-2-ethoxyethyl triflate (9.3 g, 0.0267 moles, prepared as in Example 2) was added and the solution was heated to reflux. After 1 hour, the reaction mixture was cooled to room temperature. The contents of the flask were poured into a separatory funnel containing water (50 mL). The resulting layers were separated, and the aqueous layer was extracted twice with toluene (20 mL). The combined organic layers were then washed three times with water, treated with silica gel (5 g) for one hour and filtered. After solvent removal on a rotary evaporator, a light brown oil resulted. This oil was chromatographed on silica gel (125 g), eluting with chloroform. A pale yellow semisolid (liquid crystalline at room temperature) resulted. The yield of the desired product, 5-octyl-2-(4-(1,1-dihydroheptafluoro-2-ethoxyethoxy)phenyl)pyrimidine, Compound 2, Table 1, was 6.4 g.

EXAMPLE 38

A 100 mL 3-neck flask fitted with a magnetic stir bar, septum, stopper, and water cooled condenser connected to a nitrogen bubbler was charged with 60% sodium hydride/mineral oil (0.8 g, 0.02 moles), toluene (15 mL), and dimethyl formamide (15 mL). With vigorous stirring, 5-octyl-2-(4-hydroxyphenyl)pyrimidine (3.76 g, 0.0132 moles) was added slowly to control the hydrogen evolution. The resulting mixture was stirred at room temperature for 30 minutes. Then, 1,1-dihydroperfluoro-2-(butoxyethoxy)ethyl triflate (7.47 g, 0.0132 moles, prepared as in Example 3) was added and the solution was heated to reflux. After 1 hour, the reaction mixture was cooled to room temperature. The contents of the flask were poured into a separatory funnel containing water (50 mL). The resulting layers were separated and the aqueous layer was extracted twice with toluene (20 mL). The combined organic layers were then washed three times with water, treated with silica gel (5 g) for one hour, and filtered. After solvent removal on rotary evaporator, a light brown oil resulted. This oil was chromatographed on silica gel (125 g), eluting with chloroform. A pale yellow semisolid (liquid crystalline at room temperature) resulted. The yield of the desired product, 5-octyl-2-(4-(1,1-dihydroperfluoro-2-(2-butoxyethoxy)ethoxy)phenyl)pyrimidine, Compound 3, Table 1, was 4.7 g.

EXAMPLE 39

Product was prepared as in Example 38 except 0.585 g sodium hydride, 80% dispersion in oil and 11.0 g 1,1-dihydroperfluoro-2-butoxyethoxyethyl triflate were used and 5.0 g 5-hexyl-2-(4-hydroxyphenyl)pyrimidine was substituted for the 5-octyl-2-(4-hydroxyphenyl)-pyrimidine. The resulting product, 5-hexyl-2-(4-(1,1-dihydroperfluoro-2-(2-butoxyethoxy)ethoxy)phenyl)-pyrimidine, is Compound 4, Table 1.

EXAMPLE 40

A 50 mL flask was charged with 60% sodium hydride in mineral oil (0.2 g, 0.004 moles), toluene (10 mL), N,N-dimethylformamide (10 mL) and 5-octyl-2-(4'-hydroxybiphenyl)pyrimidine (0.00277 moles, prepared as in Example 4) under an atmosphere of dry nitrogen. The mixture was stirred at room temperature for 1.5 hours. 1,1-Dihydroheptafluoro-2-ethoxyethyl triflate (0.96 g, 0.00277 moles) was then added, and the mixture was heated to 100° C. for 1.5 hours. After cooling to room temperature, the contents of the flask were poured into a separatory funnel containing water (60 mL) and toluene (20 mL). The layers were separated and the aqueous layer was extracted twice with 20 mL of toluene. The combined organic layers were washed three times with 30 mL of water, dried with anhydrous sodium sulfate, and filtered. The solvent was removed under reduced pressure. The resulting brown solid was recrystallized from ethanol, and then flash chromatographed on silica gel, eluting with chloroform to yield 0.58 g of white solid, 5-octyl-2-(4'-(1,1-dihydroheptafluoro-2-ethoxyethoxy)biphenyl)pyrimidine (Compound 5, Table 1).

EXAMPLE 41

5-Octyl-2-(4'- (1,1-dihydroperfluoro-2-(2-butoxyethoxy) ethoxybiphenyl) pyrimidine was prepared as described in Example 40, except that 1,1-dihydroperfluoro-2- (2-1-butoxyethoxy) ethyl triflate ( 1.6 g, 0.00277 moles) was used in place of 1,1-dihydroheptafluoro-2-ethoxyethyl triflate, to yield 0.4 g of 5-octyl-2-(4'-(1,1-dihydroperfluoro-2-(2-butoxyethoxy) ethoxybiphenyl) pyrimidine (Compound 6, Table 1).

EXAMPLE 42

4-Decyloxybenzoic acid (0.45 g, 0.0016 moles) and 4-(1,1-dihydroheptafluoro-2-ethoxyethoxy)phenol (0.5 g, 0.0016 moles, prepared as in Example 5) were dissolved in dichloromethane (25 mL). 1,3-dicyclohexylcarbodiimide (0.35 g, 0.0017 moles) was added to the reaction mixture, followed by 4-(N,N-dimethylamino)-pyridine (0.05 g, 0.0004 moles). The resultant mixture was stirred at room temperature under nitrogen for 18 hours. The precipitated urea was removed from the product solution by filtration, and the filtrate was concentrated on a rotary evaporator at reduced pressure. The crude solid was purified by recrystallization from ethanol, followed by flash chromatography on silica gel, eluting with chloroform, to yield 0.12 g of the desired product, Compound 7, in Table 1.

EXAMPLES 43-53

In Examples 43-53, Compounds 8-20 of Table 1, respectively, were prepared as in Example 42, except the precursor compounds indicated below were substituted for the 4-decyloxybenzoic acid and the 4-(1,1-dihydroheptafluoro-2-ethoxyethoxy)phenol.

Example 43, compound 8, was prepared from 3-chloro-4-octyloxybenzoic acid and 4-(1,1-dihydroheptafluoro-2-ethoxyethoxy)phenol (Example 5).

Example 44, compound 9, was prepared from 3-chloro-4-octyloxybenzoic acid and 4-(1,1-dihydroperfluoro-2-(butoxyethoxy)ethoxy)phenol (Example 6).

Example 45, compound 10, was prepared from 6(4-methylhexyloxy)nicotinic acid and 4-(1,1-dihydroheptafluoro-2-ethoxyethoxy)phenol (Example 5). This product was liquid at room temperature, thus it was not recrystallized, and was simply purified by chromatography.

Example 46, compound 11, was prepared from 6(4-methylhexyloxy)nicotinic acid and 4-(1,1-dihydroperfluoro-2-(2-butoxyethoxy)ethoxy)phenol (Example 6). This product was liquid at room temperature, thus it was not recrystallized, and was simply purified by chromatography.

Example 47, compound 12, was prepared from octyloxybenzoic acid and 6-(1,1-dihydroheptafluoro-2-ethoxyethoxy)-2-hydroxynapthalene (Example 9).

Example 48, compound 13, was prepared from decyloxybenzoic acid and 6-(1,1-dihydroheptafluoro-2-ethoxyethoxy)-2-hydroxynapthalene (Example 9).

Example 49, compound 14, was prepared from decyloxybenzoic acid and 6-(1,1-dihydroperfluoro-2-(2-butoxyethoxy)ethoxy)-2-hydroxynapthalene (Example 10).

Example 50, compound 15, was prepared from octyloxybenzoic acid and 4'-(1,1-dihydroheptafluoro-2-ethoxyethoxy)-4-hydroxybiphenyl (Example 7).

Example 51, compound 16, was prepared from decyloxybenzoic acid and 4,-(1,1-dihydroheptafluoro-2-ethoxyethoxy)-4-hydroxybiphenyl (Example 7).

Example 52, compound 17, was prepared from decyloxybenzoic acid and 4,-(1,1-dihydroprefluoro-2-(2-butoxyethoxy)ethoxy)-4-hydroxybiphenyl (Example 8).

Example 53, compound 18, was prepared from 4-(1,1-dihydroheptafluoro-2-ethoxyethoxy)benzoic acid (Example 11) and hydroquinone mono-trans-4-pentylcyclohexanecarboxylate.

EXAMPLE 54

2,3-Dicyano-4-octyloxyphenol (0.8 g, 0.0030 mole, Example 12), 1,1-dihydroheptafluoro-2-ethoxyethoxy)-benzoic acid (1.0 g, 0.0030 mole, Example 11) and dichloromethane (50 mL) were placed into a 100 mL round bottom flask under a dry nitrogen atmosphere. 1,3-Dicyclohexylcarbodiimide (0.64 g, 0.0031 mole) and a few crystals of 4-(N,N-dimethylamino)pyridine were added with stirring. Stirring was continued for four hours at room temperature. The resulting mixture was then filtered to remove precipitated urea that had formed. In a separatory funnel, the clear filtrate was washed with dilute hydrochloric acid, dilute potassium carbonate and water. After drying with anhydrous magnesium sulfate, the solution was again filtered and the solvent was removed on a rotary evaporator to yield a white solid. The solid was then flash chromatographed on silica gel (80 g), eluting with dichloromethane to isolate the desired product, 2,3-dicyano-4- octyloxyphenyl-4-(1,1-dihydroheptafluoroethylethoxy)benzoate, Compound 19, Table 1.

EXAMPLE 55

2,3-Difluoro-4-octyloxyphenol (0.92 g, 0.0036 mole, Example 13), 4-(1,1-dihydroheptafluoroethyl-ethocy)-benzoic acid (1.2 g, 0.0036 mole, Example 11) and dichloromethane (60 mL) were placed into a 100 mL round bottom flask under a dry nitrogen atmosphere. 1,3-Dicyclohexylcarbodiimide (0.77 g, 0.0037 mole) and a few crystals of 4-(N,N-dimethylamino)pyridine were added with stirring. Stirring was continued for four hours at room temperature. The resulting mixture was then filtered to remove precipitated urea that had formed. In a separatory funnel, the clear filtrate was washed with dilute hydrochloric acid, dilute potassium carbonate and water. After drying with anhydrous magnesium sulfate, the solution was again filtered and the solvent was removed on a rotary evaporator to yield a white solid. The solid was then flash chromatographed on silica gel (80 g), eluting with dichloromethane to isolate the desired product, 2,3-difluoro-4-octyloxyphenyl- 4-(1,1-dihydroheptafluoroethoxyethoxy)benzoate (1.2 g), Compound 20, Table 1.

COMPARATIVE EXAMPLES 1-5

In Comparative Example 1, Compound $C_1$, Table 1, was prepared using the procedure used to prepare Compound 7, except 4-(1,1-dihydroperfluorobutoxy)phenol was used in place of 4-(1,1-dihydroheptafluoro-2-ethoxyethoxy)phenol.

In comparative Example 2, Compound $C_2$, Table 1, was prepared using the procedure used to prepare Compound 10, except 4-(1,1-dihydroheptafluorobutoxy)-phenol was used in place of 4-(1,1-dihydro-heptafluoro-2-ethoxyethoxy)phenol.

In Comparative Example 3, Compound $C_3$, Table 1, was prepared using the procedure used to prepare Compound 13, except 6-(1,1-dihydroperfluorobutoxy)-2-naphthol was used in place of 6-(1,1-dihydroheptafluoro-2-ethoxyethoxy)-2-hydroxynaphthalene.

In Comparative Example 4, Compound $C_4$, Table 1, was prepared using the procedure of Example 37 except 1,1-dihydroperfluorobutyl triflate was substituted for 1,1-dihydroheptafluoro-2-ethoxyethyl triflate.

In Comparative Example 5, Compound $C_5$, Table 1, was prepared using the procedure of Example 37 except 1,1-dihydroperfluorohexyl triflate was substituted for 1,1-dihydroheptafluoro-2-ethoxyethyl triflate.

TABLE 1

| Compound | Structure |
|---|---|
| 1 | 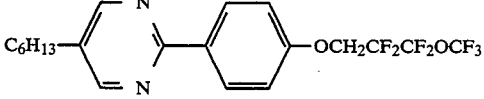 |
| 2 | 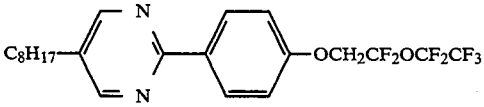 |
| 3 | 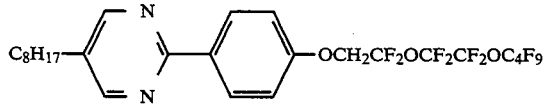 |
| 4 | 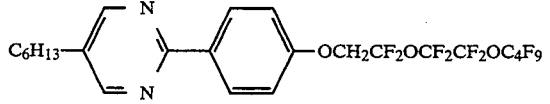 |
| 5 | 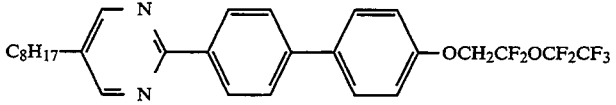 |
| 6 | 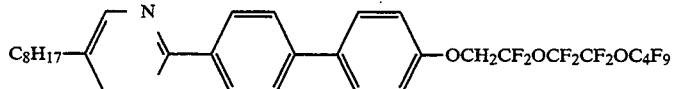 |
| 7 | 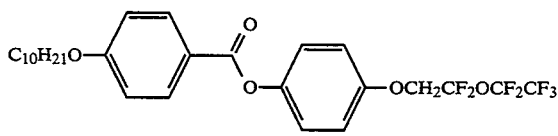 |

TABLE 1-continued

| Compound | Structure |
|---|---|
| 8 | C$_8$H$_{17}$O—(3-Cl-C$_6$H$_3$)—C(O)O—(C$_6$H$_4$)—OCH$_2$CF$_2$OCF$_2$CF$_3$ |
| 9 | C$_8$H$_{17}$O—(3-Cl-C$_6$H$_3$)—C(O)O—(C$_6$H$_4$)—OCH$_2$CF$_2$OCF$_2$CF$_2$OC$_4$F$_9$ |
| 10 | CH$_3$CH$_2$CH(CH$_3$)(CH$_2$)$_3$—O—(pyridine)—C(O)O—(C$_6$H$_4$)—OCH$_2$CF$_2$OCF$_2$CF$_3$ |
| 11 | CH$_3$CH$_2$CH(CH$_3$)(CH$_2$)$_3$—O—(pyridine)—C(O)O—(C$_6$H$_4$)—OCH$_2$CF$_2$OCF$_2$CF$_2$OC$_4$F$_9$ |
| 12 | C$_8$H$_{17}$O—(C$_6$H$_4$)—C(O)O—(naphthalene)—OCH$_2$CF$_2$OCF$_2$CF$_3$ |
| 13 | C$_{10}$H$_{21}$O—(C$_6$H$_4$)—C(O)O—(naphthalene)—OCH$_2$CF$_2$OCF$_2$CF$_3$ |
| 14 | C$_{10}$H$_{21}$O—(C$_6$H$_4$)—C(O)O—(naphthalene)—OCH$_2$CF$_2$OCF$_2$CF$_2$OC$_4$F$_9$ |
| 15 | C$_8$H$_{17}$O—(C$_6$H$_4$)—C(O)O—(C$_6$H$_4$)—(C$_6$H$_4$)—OCH$_2$CF$_2$OCF$_2$CF$_3$ |
| 16 | C$_{10}$H$_{21}$O—(C$_6$H$_4$)—C(O)O—(C$_6$H$_4$)—(C$_6$H$_4$)—OCH$_2$CF$_2$OCF$_2$CF$_3$ |

TABLE 1-continued

| Compound | Structure |
|---|---|
| 17 | $C_{10}H_{21}O$—⟨benzoate⟩—⟨biphenyl⟩—$OCH_2CF_2OCF_2CF_2OC_4F_9$ |
| 18 | $C_5H_{11}$—⟨cyclohexyl-CO-O⟩—⟨phenyl⟩—⟨O-CO⟩—⟨phenyl⟩—$OCH_2CF_2OCF_2CF_3$ |
| 19 | $C_8H_{17}O$—⟨phenyl (2,3-diCN)⟩—O-CO—⟨phenyl⟩—$OCH_2CF_2OCF_2CF_3$ |
| 20 | $C_8H_{17}O$—⟨phenyl (2,3-diF)⟩—O-CO—⟨phenyl⟩—$OCH_2CF_2OCF_2CF_3$ |
| C1 | $C_{10}H_{21}O$—⟨benzoate⟩—⟨phenyl⟩—$OCH_2CF_2CF_2CF_3$ |
| C2 | $CH_3CH_2CH(CH_3)(CH_2)_3$—O—⟨pyridyl-CO-O⟩—⟨phenyl⟩—$OCH_2CF_2CF_2CF_3$ |
| C3 | $C_{10}H_{21}O$—⟨benzoate⟩—⟨naphthyl⟩—$OCH_2CF_2CF_2CF_3$ |
| C4 | $C_8H_{17}$—⟨pyrimidinyl⟩—⟨phenyl⟩—$OCH_2C_3F_7$ |
| C5 | $C_8H_{17}$—⟨pyrimidinyl⟩—⟨phenyl⟩—$OCH_2C_5F_{11}$ |

The compounds of Table 1 were evaluated for transition temperatures by optical observation of material phase changes using a Linkam TMH600 hot stage and a Zeiss polarizing microscope. The transition temperatures (°C.), upon cooling from the isotropic state (I) to the crystalline state (K), are set forth in Table 2.

TABLE 2

| Compound No. | I to SmA | to SmC | to SmE | to M | to K |
|---|---|---|---|---|---|
| 1 | 83 | | | 1 | |
| 2 | 67 | 26 | | | 7 |
| 3 | 74 | 47 | | | −5 |
| 4 | 60 | 22 | | −15 | |
| 5 | 200 | 151 | | 66 | 64 |

TABLE 2-continued

| Compound No. | I to SmA | to SmC | to SmE | to M | to K |
|---|---|---|---|---|---|
| 6 | 208 | 158 | 145 | 51 | 42 |
| 7 | 72.8 | 63.3 | | | 37.7 |
| C1 | 87 | 61 | | | 42 |
| 8 | | | | | 36 |
| 9 | 65 | | | | 37 |
| 10 | (virtual SmA at 6 on rapid cooling) | | | | 22 |
| C2 | 43 | | | | 30 |
| 11 | 27 | | | | <−43 |
| 12 | 131 | 62 | 50 | | 36 |
| 13 | 128 | 81 | | | 44 |
| C3 | 137 | 91 | | | 44 |
| 14 | 148 | 97 | | 51 | 44 |
| 15 | 222 | 145 | 105 | 85 | |
| 16 | 186 | 136 | 121 | 105 | |
| 17 | 189 | 158 | | | 92 |
| 18 | 189 | 113 | | 97 | 83 |
| 19 | | | | 106 | |
| 20 | | | | 63 | |

As can be in comparing Compound 7 to Compound C1, Compound 10 to Compound C2 and Compound 13 to Compound C3, the compounds of the present invention having perfluoroether terminal portions have lower transition temperatures for I to SmA than do similar compounds not having the ether group in the perfluoro terminal portion.

Figure 2:
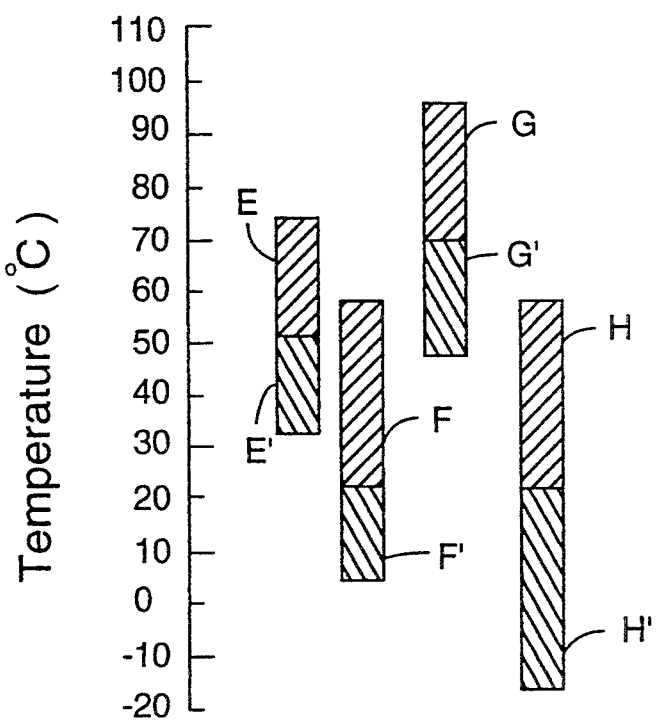
FIG. 2 shows comparative Smectic A and Smectic C phases for prior art liquid crystal materials and liquid crystal materials of the invention as determined by optical microscopy.

That the compounds of the present invention have lower transition temperatures, particularly with regard to the Smectic A and Smectic C mesophases, is further shown in FIGS. 1 and 2 where the phases were determined using DSC and optical microscopy, respectively.

In FIG. 1:
A is the Smectic A phase for Compound C4,
A' is the Smectic C phase for Compound C4,
B is the Smectic A phase for Compound 2,
B' is the Smectic C phase for Compound 2,
C is the Smectic A phase for Compound C5,
C' is the Smectic C phase for Compound C5,
D is the Smectic A phase for Compound 3, and
D' is the Smectic C phase for Compound 3.

In FIG. 2:
E is the Smectic A phase for Compound C4,
E' is the Smectic C phase for Compound C4,
F is the Smectic A phase for Compound 2,
F' is the Smectic C phase for Compound 2,
G is the Smectic A phase for Compound C5,
G' is the Smectic C phase for Compound C5,
H is the Smectic A phase for Compound 3, and
H' is the Smectic C phase for Compound 3.

EXAMPLE 56 AND COMPARATIVE EXAMPLE C6

In Example 56, a liquid crystal mixture was prepared containing

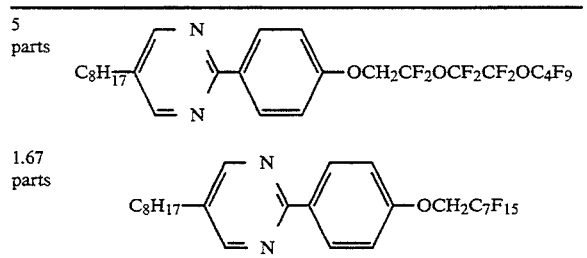

The mixture was evaluated for transition temperatures by optical observation of material phase changes using a Linkam TMH600 hot stage and a Zeiss polarizing microscope. The results are set forth in Table 3.

In Comparative Example 6, a mixture was prepared as in Example 56 except the liquid crystal material having the perfluoroether terminal portion was omitted. The mixture was evaluated for transition temperatures as in Example 56. The results are set forth in Table 3.

TABLE 3

| | Transition Temperatures (°C.) | | |
|---|---|---|---|
| Example | I to SmA | SmA to SmC | SmC to K |
| 56 | 89 | 59 | 23 |
| C6 | 111 | 84 | 69 |

As can be seen from the data in Table 3, addition of the liquid crystal material having the perfluoroether terminal portion significantly lowered the transition temperatures.

EXAMPLE 57

Product was prepared as described in Example 38 except 1,1-dihydroperfluoro-2-(2-hexyloxyethoxy)ethyl triflate (Example 14) was substituted for the 1,1-dihydroperfluoro-2-(2-butoxyethoxy)ethyl triflate. The product was purified by chromatography and then recrystallized from ethanol at −20° C. to give a white powder, 5-octyl-2-(4-(1,1-dihydroperfluoro-2-(2-hexyloxyethoxy)ethoxy)phenyl pyrimidine, Compound 21, Table 4.

EXAMPLE 58

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-2-(2-hexyloxyethoxy)ethyl triflate (Example 14) was substituted for the 1,1-dihydroperfluoro-2-(2-butoxyethoxy)ethyl triflate. The product was purified by chromatography and then recrystallized from ethanol at −20° C. to give a white powder, 5-Decyl-2-(4-(1,1-dihydroperfluoro-2-(2-hexyloxyethoxy)ethoxy)phenyl pyrimidine, Compound 22, Table 4.

EXAMPLE 59

Product was prepared as described in Example 38 except 1,1-dihydroperfluoro-4-(4-butoxybutoxy)butyl triflate (Example 15) was substituted for the 1,1-dihydroperfluoro-2-(2-butoxyethoxy)ethyl triflate. The product was purified by chromatography and then recrystallized and filtered from ethanol at −78° C. to give a white pearlescent paste at room temperature, 5-octyl- 2(4-(1,1-dihydroperfluoro-4-(4-butoxybutoxy)butoxy)-phenyl pyrimidine, Compound 23, Table 4.

EXAMPLE 60

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-4-(4-butoxybutoxy)butyl triflate (Example 15) was substituted for the 1,1-dihydroperfluoro-2-(2-butoxyethoxy)ethyl triflate. The product was purified by chromatography and then recrystallized and filtered from ethanol at −78° C. to give a white pearlescent paste at room temperature, 5-decyl-2(4-(1,1-dihydroperfluoro-4-(4-butoxybutoxy)butoxy)-phenyl pyrimidine, Compound 24, Table 4.

EXAMPLE 61

Product was prepared as described in Example 38 except 1,1-dihydroperfluoro-2-(2(2-methoxyethoxy)ethoxy)ethyl triflate (Example 16) was substituted for the 1,1-dihydroperfluoro-2-(2-butoxyethoxy)ethyl triflate. The product was purified by chromatography and then recrystallized and filtered from ethanol at −78° C. to give a white pearlescent paste at room temperature, 5-octyl-2-(4-(1,1-dihydroperfluoro-4-(2-(2-methoxyethoxy)ethoxy)ethoxy)phenyl pyrimidine, Compound 25, Table 4.

EXAMPLE 62

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-2-(2-(2methoxyethoxy)ethoxy)ethyl triflate (Example 16) was substituted for the 1,1-dihydroperfluoro-2-(2-butoxyethoxy)ethyl triflate. The product was purified by chromatography and then recrystallized and filtered from ethanol at −78° C. to give a white pearlescent paste at room temperature, 5-decyl-2-(4-(1,1-dihydroperfluoro-2-(2-(2-methoxyethoxy)ethoxy)ethoxy)phenyl pyrimidine, Compound 26, Table 4.

EXAMPLE 63

Product was prepared as described in Example 38 except 1,1-dihydroperfluoro-3-(butoxy)propyl triflate (Example 17) was substituted for the 1,1-dihydroperfluoro-2-(2-butoxyethoxy)ethyl triflate. The product was purified by chromatography and then recrystallized from ethanol at −15° C. to give a white solid, 5-octyl-2-(4-(1,1-dihydroperfluoro-3-(butoxy)propoxy)-phenyl pyrimidine, Compound 27, Table 4.

EXAMPLE 64

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-3-(butoxy)propyl triflate (Example 17) was substituted for the 1,1-dihydroperfluoro-3-(butoxy)propyl triflate. The product was purified by chromatography and then recrystallized from ethanol at −15° C. to give a white solid, 5-decyl-2-(4-(1,1-dihydroperfluoro-3-(butoxy)propoxy)phenyl pyrimidine, Compound 28, Table 4.

EXAMPLE 65

Product was prepared as described in Example 38 except 1,1-dihydroperfluoro-4-(butoxy)butyl triflate (Example 18) was substituted for the 1,1-dihydroperfluoro-2-(2-butoxyethoxy)ethyl triflate. The product was purified by chromatography and then recrystallized and filtered from ethanol at −15° C. to give a white paste, 5-octyl-2-(4-(1,1-dihydroperfluoro-4-(butoxy)butoxy)phenyl pyrimidine, Compound 29, Table 4.

EXAMPLE 66

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-4-(butoxy)butyl triflate (Example 18) was substituted for the 1,1-dihydroperfluoro-3-(butoxy)propyl triflate. The product was purified by chromatography and then recrystallized from ethanol at −15° C. to give a white solid, 5-decyl-2-(4-(1,1-dihydroperfluoro-4-(butoxy)butoxy)phenyl pyrimidine, Compound 30, Table 4.

EXAMPLE 67

Product was prepared as described in Example 38 except 1,1-dihydroperfluoro-3-(hexyloxy)propyl triflate (Example 19) was substituted for the 1,1-dihydroperfluoro-2-(2-butoxyethoxy)ethyl triflate. The product was purified by chromatography and then recrystallized and filtered from ethanol at −15° C. to give a white solid, 5-octyl-2-(4-(1,1-dihydroperfluoro-3-(hexyloxy)propoxy)phenyl pyrimidine, Compound 31, Table 4.

EXAMPLE 68

Product was prepared as described in Example 38 except 5-decyl-2-(4-hydroxyphenyl)pyrimidine was substituted for the 5-octyl-2-(4-hydroxyphenyl)pyrimidine and 1,1-dihydroperfluoro-3-(hexyloxy)propyl triflate (Example 19) was substituted for the 1,1-dihydroperfluoro-3-(butoxy)propyl triflate. The product was purified by chromatography and then recrystallized from ethanol at −15° C. to give a white solid, 5-decyl-2-(4-(1,1-dihydroperfluoro-3-(hexyloxy)propoxy)phenyl pyrimidine, Compound 32, Table 4.

EXAMPLE 69

Product was prepared as described in Example 38 except 1,1-dihydroperfluoro-3-(octyloxy)propyl triflate (Example 20) was substituted for the 1,1-dihydroperfluoro- 2-(2-butoxyethoxy)ethyl triflate. The product was purified by chromatography and then recrystallized and filtered from ethanol at room temperature to give a white solid, 5-octyl-2-(4-(1,1-dihydroperfluoro-3-(octyloxy)propoxy)phenyl pyrimidine, Compound 33, Table 4.

EXAMPLE 70

Product was prepared as described in Example 38 except 1,1-dihydroperfluoro-3-(decyloxy)propyl triflate (Example 21) was substituted for the 1,1-dihydroperfluoro-2-(2-butoxyethoxy)ethyl triflate. The product was purified by chromatography and then recrystallized and filtered from ethanol at room temperature to give a white solid, 5-octyl-2-(4-(1,1-dihydroperfluoro-3-(octyloxy)propoxy)phenyl pyrimidine, Compound 34, Table 4.

EXAMPLE 71

Product was prepared as described in Example 38 except 1,1-dihydroperfluoro-3-(neopentoxy)propyl triflate (Example 22) was substituted for the 1,1-dihydroperfluoro-2-(2-butoxyethoxy)ethyl triflate. The product was purified by chromatography and then recrystallized and filtered from ethanol at −15° C. to give a white solid, 5-octyl-2-(4-(1,1-dihydroperfluoro-3-(neopentoxy)propoxy)phenyl pyrimidine, Compound 35, Table 4.

EXAMPLE 72

Product was prepared as described in Example 38 except 2[1,1-dihydroperfluoro-2-(2butoxyethoxy)ethoxy]ethyl-p-toluenesulfonate (Example 23) was substituted for the 1,1-dihydroperfluoro-2-(2-butoxyethoxy)ethyl triflate. The product was purified by chromatography and then recrystallized and filtered from ethanol at room temperature to give a white solid, 5-octyl-2-(4-(2-[1,1-dihydroperfluoro-2-(2-butoxyethoxy)ethoxy] ethoxy)phenyl pyrimidine, Compound 36, Table 4.

EXAMPLE 73

Product was prepared as described in Example 38 except 1-bromo-2-(1,1-dihydroperfluorooctyloxy)ethane (Example 27) was substituted for the 1,1-dihydroperfluoro-2-(2-butoxyethoxy)ethyl triflate. The product was purified by chromatography and then recrystallized from ethanol at room temperature to give a white solid, 5-octyl-2-(4-(1,1-dihydroperfluorooctyloxy)ethoxy)phenyl pyrimidine, Compound 37, Table 4.

EXAMPLE 74

Product was prepared as described in Example 38 except 1-bromo-2-(1,1-dihydroperfluorohexyloxy)ethane (Example 28) was substituted for the 1,1-dihydroperfluoro-2-(2-butoxyethoxy)ethyl triflate. The product was purified by chromatography and then recrystallized from ethanol at room temperature to give a white solid, 5-octyl-2-(4-(2-(1,1-dihydroperfluorohexyloxy)ethoxy)phenyl pyrimidine, Compound 38, Table 4.

EXAMPLE 75

Product was prepared as described in Example 38 except 1-bromo-2-(2-(1,1-dihydroperfluorooctyloxy)ethoxy)ethane (Example 29) was substituted for the 1,1-dihydroperfluoro-2-(2-butoxyethoxy)ethyl triflate. The product was purified by chromatography and then recrystallized and filtered from ethanol at −15° C. to give a white solid, 5-octyl-2-(4-(2-(2-(1,1-dihydroperfluorooctyloxy)ethoxy)ethoxy)phenyl pyrimidine, Compound 39, Table 4.

EXAMPLE 76

5-Hydroxy-2-(4-(1,1-dihydroperfluoro-2-(butoxyethoxy)ethoxy)phenyl) pyrimidine (10 g, 0.0166 mol, Example 32) was dissolved in 150 mL of N,N-dimethylformamide and slowly treated with 0.5 g dry sodium hydride. After 15 minutes stirring, 1-bromodecane (3.67 g, 0.0166 mol) was added and the mixture was heated to 100° C. for 2 hours. Upon cooling to room temperature, 150 mL water was added and a solid precipitated. The solid was collected by filtration, recrystallized from ethanol and chromatographed on 150 g silica gel (chloroform), to yield 4.0 g, Compound 40, Table 4.

EXAMPLES 77–81

In Examples 77–81, Compounds 40–44 of Table 1 were prepared as in Example 76, except that the precursor compounds indicated below were substituted for the 5-hydroxy-2-(4-(1,1-dihydroperfluoro-2(butoxyethoxy)ethoxy)phenyl)pyrimidine and 1 -bromodecane.

Example 77, Compound 41 was prepared from 5-hydroxy-2-(4-(1,1-dihydroperfluoro-2(butoxyethoxy)ethoxy)phenylpyrimidine (Example 32) and 1-bromooctane.

Example 78, Compound 42 was prepared from 5-hydroxy-2-(4-(1,1-dihydroperfluoro-2-(butoxy)ethoxy)-phenyl) pyrimidine (Example 33) and 1-bromooctane.

Example 79, Compound 43 was prepared from 5-hydroxy-2-(4-(octyloxy)phenyl)pyrimidine (Example 34) and 1,1-dihydroperfluro-2-(butoxy)ethyltriflate.

Example 80, Compound 44 was prepared from 5-hydroxy-2-(4-(octyloxy)phenyl)pyrimidine (Example 34) and 1,1-dihydroperfluro-2-(butoxyethoxy)ethyltriflate.

Example 81, Compound 45 was prepared from 5-hydroxy-2-(4′-(1,1-dihydroperfluoro-2-(butoxyethoxy)ethoxy)bisphenol)pyrimidine (Example 35) and 1-bromo-2-(butoxyethoxy)ethane.

TABLE 4

| Compound | Structure |
| --- | --- |
| 21 | $C_8H_{17}$—pyrimidine—phenyl—$OCH_2CF_2OC_2F_4OC_6F_{13}$ |
| 22 | $C_{10}H_{21}$—pyrimidine—phenyl—$OCH_2CF_2OC_2F_4OC_6F_{13}$ |
| 23 | $C_8H_{17}$—pyrimidine—phenyl—$OCH_2C_3F_6OC_4F_8OC_4F_9$ |
| 24 | $C_{10}H_{21}$—pyrimidine—phenyl—$OCH_2C_3F_6OC_4F_8OC_4F_9$ |

TABLE 4-continued

| Compound | Structure |
|---|---|
| 25 | $C_8H_{17}$—[pyrimidine]—[phenyl]—$OCH_2CF_2(OC_2F_4)_2OCF_3$ |
| 26 | $C_{10}H_{21}$—[pyrimidine]—[phenyl]—$OCH_2CF_2(OC_2F_4)_2OCF_3$ |
| 27 | $C_8H_{17}$—[pyrimidine]—[phenyl]—$OCH_2C_2F_4OC_4F_9$ |
| 28 | $C_{10}H_{21}$—[pyrimidine]—[phenyl]—$OCH_2C_2F_4OC_4F_9$ |
| 29 | $C_8H_{17}$—[pyrimidine]—[phenyl]—$OCH_2C_3F_6OC_4F_9$ |
| 30 | $C_{10}H_{21}$—[pyrimidine]—[phenyl]—$OCH_2C_3F_6OC_4F_9$ |
| 31 | $C_8H_{17}$—[pyrimidine]—[phenyl]—$OCH_2C_2F_4OC_6F_{13}$ |
| 32 | $C_{10}H_{21}$—[pyrimidine]—[phenyl]—$OCH_2C_2F_4OC_6F_{13}$ |
| 33 | $C_8H_{17}$—[pyrimidine]—[phenyl]—$OCH_2C_2F_4OC_8F_{17}$ |
| 34 | $C_8H_{17}$—[pyrimidine]—[phenyl]—$OCH_2C_2F_4OC_{10}F_{21}$ |
| 35 | $C_8H_{17}$—[pyrimidine]—[phenyl]—$OCH_2C_2F_4OCF_2C(CF_3)_3$ |
| 36 | $C_8H_{17}$—[pyrimidine]—[phenyl]—$OC_2H_4OCH_2CF_2OC_2F_4OC_4F_9$ |
| 37 | $C_8H_{17}$—[pyrimidine]—[phenyl]—$OC_2H_4OCH_2C_7F_{15}$ |

TABLE 4-continued

| Compound | Structure |
|---|---|
| 38 | C8H17—[pyrimidine]—[phenyl]—OC2H4OCH2C5F11 |
| 39 | C8H17—[pyrimidine]—[phenyl]—OC2H4OC2H4OCH2C7F15 |
| 40 | C10H21O—[pyrimidine]—[phenyl]—OCH2CF2OCF2CF2OC4F9 |
| 41 | C8H17O—[pyrimidine]—[phenyl]—OCH2CF2OCF2CF2OC4F9 |
| 42 | C8H17O—[pyrimidine]—[phenyl]—OCH2CF2OC4F9 |
| 43 | C8H17O—[phenyl]—[pyrimidine]—OCH2CF2OC4F9 |
| 44 | C8H17O—[phenyl]—[pyrimidine]—OCH2CF2OCF2CF2OC4F9 |
| 45 | C4H9OCH2CH2OCH2CH2O—[pyrimidine]—[phenyl]—[phenyl]—OCH2CF2OCF2CF2OC4F9 |

The compounds of Table 4 were evaluated for transition temperatures by optical observation of material phase changes using a Linkam TMH600 hot stage and Zeiss polarizing microscope. The transition temperatures (°C.), upon cooling from the isotropic state (I) to the crystalline state (K), are set forth in Table 5.

TABLE 5

| Compound No. | I to SmA | to SmC | to M | to K |
|---|---|---|---|---|
| 21 | 79 | 52 | — | 23 |
| 22 | 65 | 50 | — | 18 |
| 23 | 103 | 53 | — | −11 |
| 24 | 94 | 60 | — | 13 |
| 25 | 81 | 50 | 24 | −5 |
| 26 | 60 | 43 | −6 | −17 |
| 27 | 82 | 47 | — | 7 |
| 28 | 67 | 55 | — | 28 |
| 29 | 104 | 57 | — | −9 |
| 30 | 88 | 61 | — | 16 |
| 31 | 88 | 52 | — | 15 |
| 32 | 73 | 55 | — | 48 |
| 33 | 95 | — | — | 60 |
| 34 | 98 | — | — | 94 |
| 35 | 82 | 48 | — | 24 |
| 36 | 109 | — | — | 3 |
| 37 | 132 | — | — | 69 |
| 38 | 123 | — | — | 74 |
| 39 | 92 | — | — | 48 |
| 40 | 87 | 74 | — | 24 |
| 41 | 94 | 81 | — | 45 |
| 42 | 96 | 78 | — | 46 |
| 43 | — | — | — | 88 |
| 44 | 94 | — | — | 73 |
| 45 | 182 | 107 | 84 | 81 |

Various modifications and alterations of this invention will become apparent to those skilled in the art without departing from the scope of the invention.

What is claimed is:

1. Fluorine-containing achiral liquid crystal compounds comprising a fluorocarbon terminal portion having at least one catenary ether oxygen located between two flurocarbons and a hydrocarbon terminal portion, the terminal portions being connected by a central core, the compounds having smectic mesophases or having latent smectic mesophases.

2. Compounds of claim 1 wherein said fluorocarbon terminal portion can be represented by the formula $-D(C_xF_{2x}O)_zC_yF_{2y+1}$ where x is independently 1 to 10 for each $C_xF_{2x}O$ group, y is 1 to 10, z is 1 to 10 and D is a covalent bond,

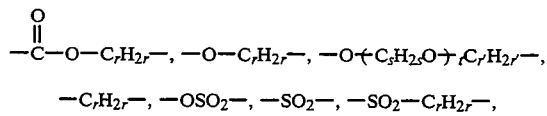

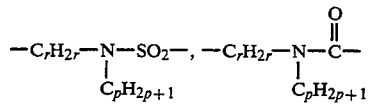

where r and r' are independently 1 to 20, s is independently 1 to 10 for each $(C_sH_{2s}O)$, t is 1 to 6 and p is 0 to 4.

3. A compound according to claim 1 wherein said compound can be represented by the formula

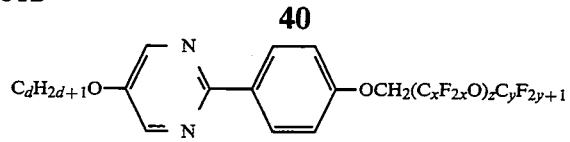

where d is 5 to 10, x is independently 1 to 3 for each $C_xF_{2x}O$ group, y is 1 to 4 and z is 1 to 3.

4. A compound according to claim 1 wherein said compound can be represented by the formula

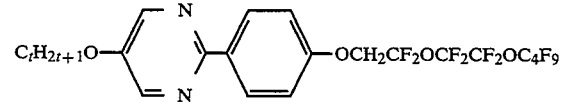

where t is 6, 8 or 10.

5. A compound according to claim 1 wherein said compound can be represented by the formula

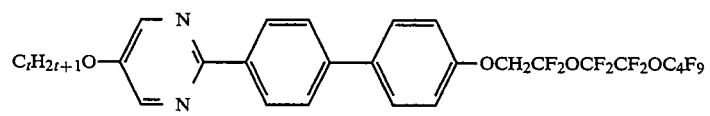

where t is 6, 8 or 10.

6. Liquid crystal mixtures comprising at least one compound according to claim 1 and at least one chiral liquid crystal compound, said chiral liquid crystal compound being present in an amount sufficient to provide the mixture with ferroelectric properties.

7. A liquid crystal display device containing said compound of claim 1 wherein said compound has a smectic mesophase.

* * * * *

UNITED STATES PATENT AND TRADEMARK OFFICE
CERTIFICATE OF CORRECTION

PATENT NO. : 5,437,812
DATED : August 1, 1995
INVENTOR(S) : Eugene P. Janulis, Patricia M. Savu, Terence D. Spawn, and Mark D. Radcliffe It is certified that error appears in the above-indentified patent and that said Letters Patent is hereby corrected as shown below:

Col. 2, line 43  "X-(CF$_2$)n-(CH$_2$)$_m$-Q-" should read -- X-(CF$_2$)$_n$-(CH$_2$)$_m$-Q- --

Col. 8, line 64  "—the," should read -- —TeH, --

Col. 9, lines 29-32
$$\text{"} -CH_2)_r-\underset{\underset{C_pH_{2p+1}}{|}}{N}-\overset{\overset{O}{\|}}{C}- \text{"} \quad \text{should read} \quad -- -C_rH_{2r}-\underset{\underset{C_pH_{2p+1}}{|}}{N}-\overset{\overset{O}{\|}}{C}- --$$

Col. 16, line 58  " (C$_{10}$F$_{21}$OC$_2$F$_4$CH$_{20}$SO$_2$CF$_3$, " should read
-- (C$_{10}$F$_{21}$OC$_2$F$_4$CH$_2$SO$_2$CF$_3$, --

Col. 22, line 40  " 4,-(1,1-dihydroheptafluoro-2- " should read
-- 4'-(1,1-dihydroheptafluoro-2- --

Col. 22, line 43  " 4,-(1,1-dihydroperfluoro-2-(2- " should read
- "4,-(1,1-dihydroprefluoro-2-(2-".

Col. 23, line 6  at end of sentance " -ethocy)- " should read -- ethoxy)- --

Col. 24, line 3  " C$_1$ " should read -- C1 --

Col. 24, line 8  " C$_2$ " should read -- C2 --

Col. 24, line 13  " C$_3$ " should read -- C3 --

Col. 24, line 18  " C$_4$ " should read -- C4 --

UNITED STATES PATENT AND TRADEMARK OFFICE
CERTIFICATE OF CORRECTION

PATENT NO. : 5,437,812
DATED : August 1, 1995
INVENTOR(S) : Eugene P. Janulis, Patricia M. Savu, Terence D. Spawn, and Mark D. Radcliffe It is certified that error appears in the above-indentified patent and that said Letters Patent is hereby corrected as shown below:

Col. 24, line 22   " $C_5$ " should read -- C5 --

Col. 34, line 24   " 5-hydroxy-2-(4-(1,1-dihydroperfluoro-2(butoxyethoxy)3- "

should read

--5-hydroxy-2-(4-(1,1-dihydroperfluoro-2-(butoxyethoxy)---

Col. 34, line 27   " hydroxy-2-(4-(1,1-dihydrroperfluoro-2(butoxyethoxshould read --hydroxy-2-(4-(1,1-dihydroperfluoro-2-(butoxyethox--

Col. 34, line 28   " y)ethoxy)phenylpyrimidine "

should read -- y)ethoxy)phenyl)pyrimidine --

Col. 39, lines 28-34   Move these lines from this column to Col. 40, line 27 (before Claim 7)

Signed and Sealed this

Nineteenth Day of December, 1995

BRUCE LEHMAN

Attest:

Attesting Officer

Commissioner of Patents and Trademarks